(12) United States Patent
Heli et al.

(10) Patent No.: US 11,371,992 B2
(45) Date of Patent: Jun. 28, 2022

(54) SOLID PHASE IMMUNOASSAY APPARATUS AND METHOD FOR RAPID DETECTION OF BACTERIA

(71) Applicant: Polyvalor, Limited Partnership, Montreal (CA)

(72) Inventors: Bentolhoda Heli, Montreal (CA); Abdellah Ajji, Mont-Royal (CA)

(73) Assignee: POLYVALOR, LIMITED PARTNERSHIP, Montréal (CA)

( * ) Notice: Subject to any disclaimer, the term of this patent is extended or adjusted under 35 U.S.C. 154(b) by 38 days.

(21) Appl. No.: 16/589,420

(22) Filed: Oct. 1, 2019

(65) Prior Publication Data

US 2020/0103404 A1    Apr. 2, 2020

Related U.S. Application Data

(60) Provisional application No. 62/740,063, filed on Oct. 2, 2018.

(51) Int. Cl.
| | |
|---|---|
| *G01N 33/53* | (2006.01) |
| *G01N 33/569* | (2006.01) |
| *G01N 33/543* | (2006.01) |
| *G01N 21/64* | (2006.01) |
| *G01N 33/58* | (2006.01) |
| *B82Y 15/00* | (2011.01) |

(52) U.S. Cl.
CPC ... *G01N 33/56911* (2013.01); *G01N 21/6428* (2013.01); *G01N 33/54306* (2013.01); *G01N 33/582* (2013.01); *G01N 33/588* (2013.01); *B82Y 15/00* (2013.01); *G01N 33/54346* (2013.01); *G01N 2021/6441* (2013.01)

(58) Field of Classification Search
None
See application file for complete search history.

(56) References Cited

U.S. PATENT DOCUMENTS

| | | | | |
|---|---|---|---|---|
| 6,228,658 | B1* | 5/2001 | Formica | G01N 33/54366 |
| | | | | 422/411 |
| 10,941,447 | B2* | 3/2021 | Dudley, Jr. | G01N 33/577 |
| 2005/0096516 | A1* | 5/2005 | Soykan | G01N 21/6452 |
| | | | | 600/317 |
| 2007/0160789 | A1* | 7/2007 | Merical | B32B 27/308 |
| | | | | 428/35.7 |
| 2017/0336398 | A1* | 11/2017 | Lin | G01N 33/553 |

OTHER PUBLICATIONS

Wang et al., FRET on lateral flow test strip to enhance sensitivity for detecting cancer biomarker, Talanta 176, 2018, pp. 444-449). (Year: 2018).*
Gerbers, Roman, Development of Enhanced Lateral Flow test Devices for Point-of-Care Diagnostics, University of Rhode Island DigitalCommons@URI, Open Access Master's Theses, 2013, pp. 1-120. (Year: 2013).*
Morales-Narvaez et al., Nanopaper as an Optical Sensing Plallrom, ACS NANO, vol. 9, No. 7, 2015, pp. 7296-7305. (Year: 2015).*
Khan et al., Nano-gold assisted highly conducting and biocomplatible bacterial cellulose-PEDOT:PSS films for biology-device interface applications, International Journal of Biological Macromolecules, 107, 2018, pp. 865-873. (Year: 2018).*
Lund et al., The occurrence and prevention of foodbome disease in vulnerable people. Foodborne Pathogens and Disease 2011, 8(9), 961-973.
Scallan et al., Foodborne illness acquired in the United States—major pathogens. Emerg Infect Dis 2011,17(1)7-15.
Zhao et al., Advances in rapid detection methods for foodborne pathogens. J. Microbiol. Biotechnol. 2014, 24(3), 297-312.
Lazcka et al., Pathogen detection: a perspective of traditional methods and biosensors. Biosensors and Bioelectronics 2007, 22(7), 1205-1217.
Kagan, At the Nexus of Food Security and Safety: Opportunities for Nanoscience and Nanotechnology. ACS Nano 2016, 10(3), 2985-2986.
Chen et al., Integrating recognition elements with nanomaterials for bacteria sensing. Chemical Society Reviews 2017, 46(5), 1272-1283.
Sutarlie et al., Nanomaterials-based biosensors for detection of microorganisms and microbial toxins. Biotechnology Journal 2016 12(4).
Vikesland et al., Nanomaterial enabled biosensors for pathogen monitoring—a review. Environmental Science & Technology 2010, 44(10), 3656-3669.
Ray et al., Nanoscopic optical rulers beyond the FRET distance limit: fundamentals and applications. Chemical Society Reviews 2014, 43(17), 6370-6404.
Morales-Narvaez et al., Graphene oxide as a pathogen-revealing agent sensing with a digital-like response. Angewandte Chemie 2013, 125(51), 14024-14028.
Ko et al., A novel FRET-based optical fiber biosensor for rapid detection of *Salmonella typhimurium*. Biosensors and Bioelectronics 2006, 21(7), 1283-1290.
Chen et al., Fluorescent nanosensors based on fluorescence resonance energy transfer (FRET). Industrial & Engineering Chemistry Research 2013, 52(33), 11228-11245.

(Continued)

*Primary Examiner* — Gary Counts
(74) *Attorney, Agent, or Firm* — McLane Middleton, Professional Association

(57) ABSTRACT

An assay device is provided for use in determining the presence of a target analyte in a sample. The assay device comprises a solid platform comprising a fibrous mat, the solid platform impregnated with a first FRET chromophore. An antibody-FRET chromophore conjugate is immobilized on a surface of the solid platform, wherein the antibody-FRET chromophore conjugate comprises an antibody affixed to a second FRET chromophore. The first FRET chromophore and the second FRET chromophore are selected to provide an energy transfer from one to another when located within a Förster distance with respect to each other, thereby forming a FRET donor-acceptor chromophore pair. In a further aspect, a method of detecting a target analyte in a sample is provided. In yet a further aspect, packaging sheet materials and packaging articles employing the assay device under certain conditions are provided.

29 Claims, 11 Drawing Sheets

(56) References Cited

OTHER PUBLICATIONS

Hötzer et al., Fluorescence in nanobiotechnology: sophisticated fluorophores for novel applications. Small 2012, 8(15), 2297-2326.
Resch-Genger et al., Quantum dots versus organic dyes as fluorescent labels. Nature Methods 2008, 5(9), 763-775.
Pons et al., On the quenching of semiconductor quantum dot photoluminescence by proximal gold nanoparticles. Nano Letters 2007, 7 (10), 3157-3164.
Hildebrandt et al., Energy transfer with semiconductor quantum dot bioconjugates: a versatile platform for biosensing, energy harvesting, and other developing applications. Chemical Reviews 2017, 117 (2), 536-711.
Morales-Narváez et al., Nanopaper as an optical sensing platform. ACS Nano 2015, 9 (7), 7296-7305.
Heli et al., Modulation of population density and size of silver nanoparticles embedded in bacterial cellulose via ammonia exposure: visual detection of volatile compounds in a piece of plasmonic nanopaper. Nanoscale 2016, 8(15), 7984-7991.
Sela-Culang et al., A systematic comparison of free and bound antibodies reveals binding-related conformational changes. The Journal of Immunology 2012, 189(10), 4890-4899.
Elgert, Immunology: Understanding the Immune System. John Wiley & Sons (1996), pp. 58-78.
Saito et al., TEMPO-mediated oxidation of native cellulose. The effect of oxidation conditions on chemical and crystal structures of the water-insoluble fractions. Biomacromolecules 2004, 5(5), 1983-1989.
Da Silva Perez et al., TEMPO-mediated oxidation of cellulose III. Biomacromolecules 2003, 4(5), 1417-1425.
Kimling et al., Turkevich method for gold nanoparticle synthesis revisited. The Journal of Physical Chemistry B 2006, 110(32), 15700-15707.
Parolo et al., Design, preparation, and evaluation of a fixed-orientation antibody/gold-nanoparticle conjugate as an immunosensing label. ACS Applied Materials & Interfaces 2013, 5(21), 10753-10759.
Iguchi et al., Bacterial cellulose—a masterpiece of nature's arts. Journal of Materials Science 2000, 35(2), 261-270.
Yamanaka et al., The structure and mechanical properties of sheets prepared from bacterial cellulose. Journal of Materials Science 1989, 24(9), 3141-3145.
Kim et al., Analysis of direct immobilized recombinant protein G on a gold surface. Ultramicroscopy 2008, 108(10), 1152-1156.
Makaraviciute et al., Site-directed antibody immobilization techniques for immunosensors. Biosensors and Bioelectronics 2013, 50, 460-471.
Lee et al., Direct immobilization of protein G variants with various numbers of cysteine residues on a gold surface. Analytical Chemistry 2007, 79(7), 2680-2687.
Jin et al., Upconversion nanoparticles based FRET aptasensor for rapid and ultrasensitive bacteria detection. Biosensors and Bioelectronics 2017, 90, 525-533.
Pourreza et al., Green in-situ synthesized silver nanoparticles embedded in bacterial cellulose nanopaper as a bionanocomposite plasmonic sensor. Biosensors and Bioelectronics 2015, 74, 353-359.

\* cited by examiner

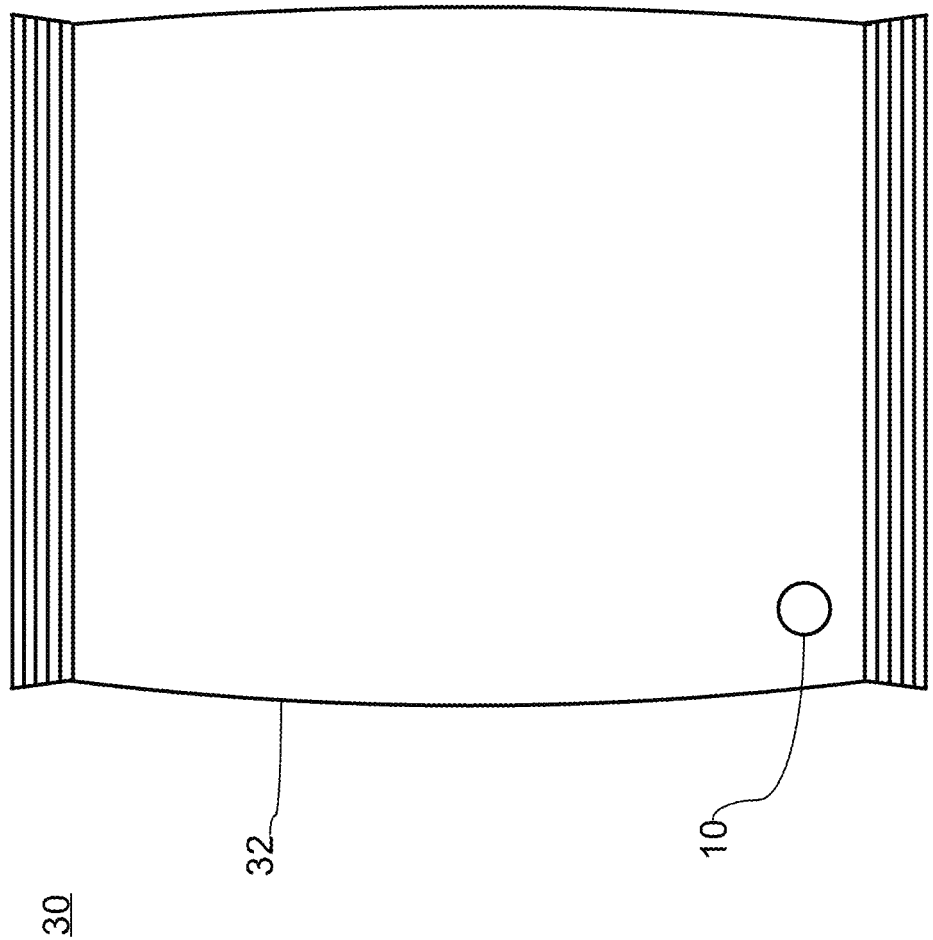

SOLID PHASE IMMUNOASSAY APPARATUS AND METHOD FOR RAPID DETECTION OF BACTERIA

CROSS-REFERENCE TO RELATED APPLICATION

This application claims the priority benefit of U.S. Provisional Application Ser. No. 62/740,063 filed Oct. 2, 2018. The aforementioned application is incorporated herein by reference in its entirety.

BACKGROUND

The present development is directed to biosensors and, more particularly, to an immunosensor developed on a solid nanofiber platform based on Förster (fluorescence) resonance energy transfer (FRET). The present immunosensor provides a new type of portable sensor, and may advantageously find utility for use in food packaging under certain conditions as well as other uses, including as sensors in the environmental and medical sectors, among others.

Generally, storage, shelf conditions, and packaging have been considered effective parameters for controlling the freshness and safety of foods. However, it cannot guarantee that food is not deteriorated or free of contamination, such as foodborne pathogens or spoilage microorganisms. As such, food quality control is necessary not only to protect customers against foodborne illness but also to minimize the waste of food resulting from microbial spoilage. Even taking into account all precautions and preservation techniques, the outbreak of foodborne diseases remains a threat to public health and has significantly increased over the last two decades. For instance, the Centers for Disease Control and Prevention (CDC) has estimated that every year 48 million people in the United States alone are infected by foodborne pathogens, leading to approximately 128,000 hospitalizations and 3,000 deaths. Therefore, rapid, accurate, and in-situ approaches for identifying, directly and/or indirectly, food deterioration, bacteria, or contamination in the food industry would be desirable to overcome these problems.

Recently, smart or intelligent food packaging (packaging integrated with a miniaturized detection device) has been proposed to meet the demands of customers and food industries, especially in early recognition techniques of pathogens or spoilage bacteria, which can reveal the necessary information about the safety of food and help consumers' decision making. These demands have created a strong driving force for the development and production of in-situ and real-time detection techniques for use as sensors applicable in food packaging. Despite efforts to design a user-friendly, sensitive, and selective sensor for detecting foodborne pathogens and food spoilage, most of them are not applicable in the food packaging industry, owing to their solution-based functionality, their need for a secondary biomarker to accomplish the recognition procedure, and the complexity of the instrumentation required to read the signal.

Outbreaks of foodborne diseases have seriously threatened people's lives worldwide and have led to a remarkable number of hospitalizations and even deaths due to the consumption of contaminated foods. Precise monitoring and early recognition of pathogens can ensure the safety of food and prevent the consequences of foodborne pathogens that have become widespread. Although there are traditional methods for detecting foodborne bacteria, the high cost, long processing time, and the need for a scientific expert have restricted their use in the food packaging industries. Therefore, to address these problems, it would be desirable to develop a fast, highly selective and sensitive, low-priced, in-situ, and user-friendly recognition device.

The present disclosure contemplates a new and improved biosensor apparatus, method, and packaging articles which overcome the above-referenced problems and others.

SUMMARY

The present disclosure is directed to a sensitive FRET-based immunosensor developed on a nanofiber platform for the detection of a foodborne pathogen, such as *Escherichia coli* (*E. coli*) bacteria. In certain embodiments, the platform is a nanopaper platform comprising carboxylated bacterial cellulose impregnated with a FRET acceptor chromophore, such as gold nanoparticles (AuNPs). An antibody against a food borne pathogen, such as *E. coli*, is conjugated to a FRET donor chromophore, such as a quantum dot (QD) or a fluorescent dye. The antibody-FRET donor conjugate is linked to an immobilization protein, such as Protein A/G or Protein A, which, in turn, is immobilized on the nanopaper platform. When a bacterium is captured by the antibody-FRET donor conjugate, energy transfer from the FRET donor to the FRET acceptor is triggered due to the reduction in the distance between the donor and acceptor as the result of the conformational change in the antibody structure.

In certain preferred embodiments, the platform is a nanopaper platform comprising carboxylated bacterial cellulose impregnated with gold nanoparticles (AuNPs). In certain preferred embodiments, the antibody-FRET donor conjugate is an anti-*E. coli* antibody conjugated to a quantum dot. Although the present development is described herein primarily by way of reference to the detection of *E. coli*, it will be recognized that the present development may also be adapted for detection of other bacteria, including food borne bacteria such as *Salmonella* (e.g., *Salmonella enterica*), *Listeria* (e.g., *Listeria monocytogenes*), and *Campylobacter*, (e.g., *Campylobacter jejuni*).

In one aspect, an assay device is provided for use in determining the presence of a target analyte in a sample. The assay device comprises a solid platform comprising a fibrous mat, the solid platform impregnated with a first FRET chromophore. An antibody-FRET chromophore conjugate is immobilized on a surface of the solid platform, wherein the antibody-FRET chromophore conjugate comprises an antibody affixed to a second FRET chromophore. The first FRET chromophore and the second FRET chromophore are selected to provide an energy transfer from one to another when located within a Förster distance with respect to each other, thereby forming a FRET donor-acceptor chromophore pair.

In more limited aspects, the fibrous mat comprises bacterial cellulose and/or carboxylated bacterial cellulose.

In more limited aspects, the fibrous mat comprises carboxylated bacterial cellulose.

In another more limited aspect, the first FRET chromophore is a FRET acceptor.

In another more limited aspect, the first FRET chromophore is a FRET quencher.

In another more limited aspect, the first FRET chromophore comprises nanoparticles selected from the group consisting of gold nanoparticles and silver nanoparticles.

In another more limited aspect, the first FRET chromophore comprises gold nanoparticles.

In another more limited aspect, the gold nanoparticles are formed within the fibrous mat in situ.

In another more limited aspect, the antibody-FRET chromophore conjugate is immobilized on the fibrous mat with a protein covalently bonded to the fibrous mat.

In another more limited aspect, the protein is bound to an Fc region of the antibody.

In another more limited aspect, the protein is selected from the group consisting of Protein A and Protein A/G.

In another more limited aspect, the protein is Protein A/G.

In another more limited aspect, the second FRET chromophore is a FRET donor.

In another more limited aspect, the second FRET chromophore is selected from the group consisting of a quantum dot and a fluorescent dye.

In another more limited aspect, the second FRET chromophore is a quantum dot.

In another more limited aspect, the second FRET chromophore is a fluorescent dye.

In another more limited aspect, the antibody is an antibody against a foodborne pathogen.

In another more limited aspect, the antibody is an antibody against a foodborne pathogen selected from the group consisting of *E. coli, Salmonella, Listeria*, and *Campylobacter*.

In a further aspect of the present development, a method of detecting a target analyte in a sample comprises combining the sample with an assay device, the assay device comprising a solid platform comprising a fibrous mat. The solid platform is impregnated with a first FRET chromophore and an antibody-FRET chromophore conjugate is immobilized on a surface of the solid platform. The antibody-FRET chromophore conjugate comprises an antibody affixed to a second FRET chromophore, wherein the first FRET chromophore and the second FRET chromophore are selected to provide an energy transfer from one to another when located within a Förster distance with respect to each other, thereby forming a FRET donor-acceptor chromophore pair. At least one FRET signal generated by the first FRET chromophore and/or second FRET chromophore is measured to detect the target analyte in the sample.

In a more limited aspect, the fibrous mat comprises one or both of bacterial cellulose and carboxylated bacterial cellulose.

In a more limited aspect, the fibrous mat comprises carboxylated bacterial cellulose.

In another more limited aspect, the first FRET chromophore is a FRET acceptor.

In another more limited aspect, the first FRET chromophore is a FRET quencher.

In another more limited aspect, the first FRET chromophore comprises nanoparticles selected from the group consisting of gold nanoparticles and silver nanoparticles.

In another more limited aspect, the first FRET chromophore comprises gold nanoparticles.

In another more limited aspect, the gold nanoparticles are formed within the fibrous mat in situ.

In another more limited aspect, the antibody-FRET chromophore conjugate is immobilized on the fibrous mat with a protein covalently bonded to the fibrous mat.

In another more limited aspect, the protein is bound to an Fc region of the antibody.

In another more limited aspect, the protein is selected from the group consisting of Protein A and Protein A/G.

In another more limited aspect, the protein is Protein A/G.

In another more limited aspect, the second FRET chromophore is FRET donor.

In another more limited aspect, the second FRET chromophore is selected from the group consisting of a quantum dot and a fluorescent dye.

In another more limited aspect, the second FRET chromophore is a quantum dot.

In another more limited aspect, the antibody is an antibody against a foodborne pathogen.

In another more limited aspect, the antibody is an antibody against a foodborne pathogen selected from the group consisting of *E. coli, Salmonella, Listeria*, and *Campylobacter*.

In a further aspect, a packaging material for detection of microbial contamination in a sample is provided. The packaging material comprises a packaging sheet material and an assay device. The assay device comprises a solid platform comprising a fibrous mat impregnated with a first FRET chromophore. An antibody-FRET chromophore conjugate is immobilized on a surface of the solid platform. The antibody-FRET chromophore conjugate comprises an antibody affixed to a second FRET chromophore. The first FRET chromophore and the second FRET chromophore are selected to provide an energy transfer from one to another when located within a Förster distance with respect to each other, thereby forming a FRET donor-acceptor chromophore pair, wherein the sample contacts the assay device, and wherein the energy transfer is configured to trigger an optically detectable change in signal in the presence of a microbial contaminant.

In another more limited aspect, the change in the energy transfer is triggered in response to a change in distance between the first FRET chromophore and the second FRET chromophore as a result of a conformational change in the antibody upon capture of a microbial contaminant.

In another more limited aspect, the sample is a food product.

In another more limited aspect, the packaging sheet material is a polymer film.

One advantage of the present invention is that it allows for integration of a biosensor into food packaging, which allows improved monitoring of food inside of the package. As such, the present development can reveal information about the food's safety, assist the consumer in their decision making, prevent consumers from buying the contaminated or deteriorated foods, prevent the outbreak of foodborne diseases, and reduce food waste.

Another advantage of the present development is that it is user-friendly for consumers. In certain embodiments, the signal can be detected and recorded with minimal instrumentation, such as a smartphone or other mobile device running an application program to record and/or display the signal.

Another advantage resided in the fact that optical detection can be sensed using readily available technology. In certain embodiments, smartphone camera technology may be used to provide an optical detection system by supporting an appropriate app.

Another advantage of the present development resides in the fact that optical detection proceeds directly after the capture of the analyte, thereby making an additional treatment or a secondary biomarker unnecessary. This, in turn, makes the present sensor highly suitable for smart packaging, especially food packaging.

Another advantage of the present invention is that the sensed output is based on an intrinsic characteristic of the antibody.

Another advantage of the present development is that in situ synthesis of nanoparticles can be employed, overcoming the problem of aggregation of nanoparticles.

Yet another advantage of the present development resides in its ability to use bacterial cellulose, which is a sustainable and biocompatible biopolymer.

Still another advantage of the present development is that it utilizes a solid-based platform.

Still further advantages and benefits of the present invention will become apparent to those of ordinary skill in the art upon reading and understanding the following detailed description of the preferred embodiments.

BRIEF DESCRIPTION OF THE DRAWING

The invention may take form in various components and arrangements of components, and in various steps and arrangements of steps. The drawings, which are not necessarily to scale, are only for purposes of illustrating preferred embodiments and are not to be construed as limiting the invention.

FIG. 11 illustrates an exemplary packaging article incorporating the assay device in accordance with the present disclosure.

DETAILED DESCRIPTION OF THE PREFERRED EMBODIMENTS

Figure 1:
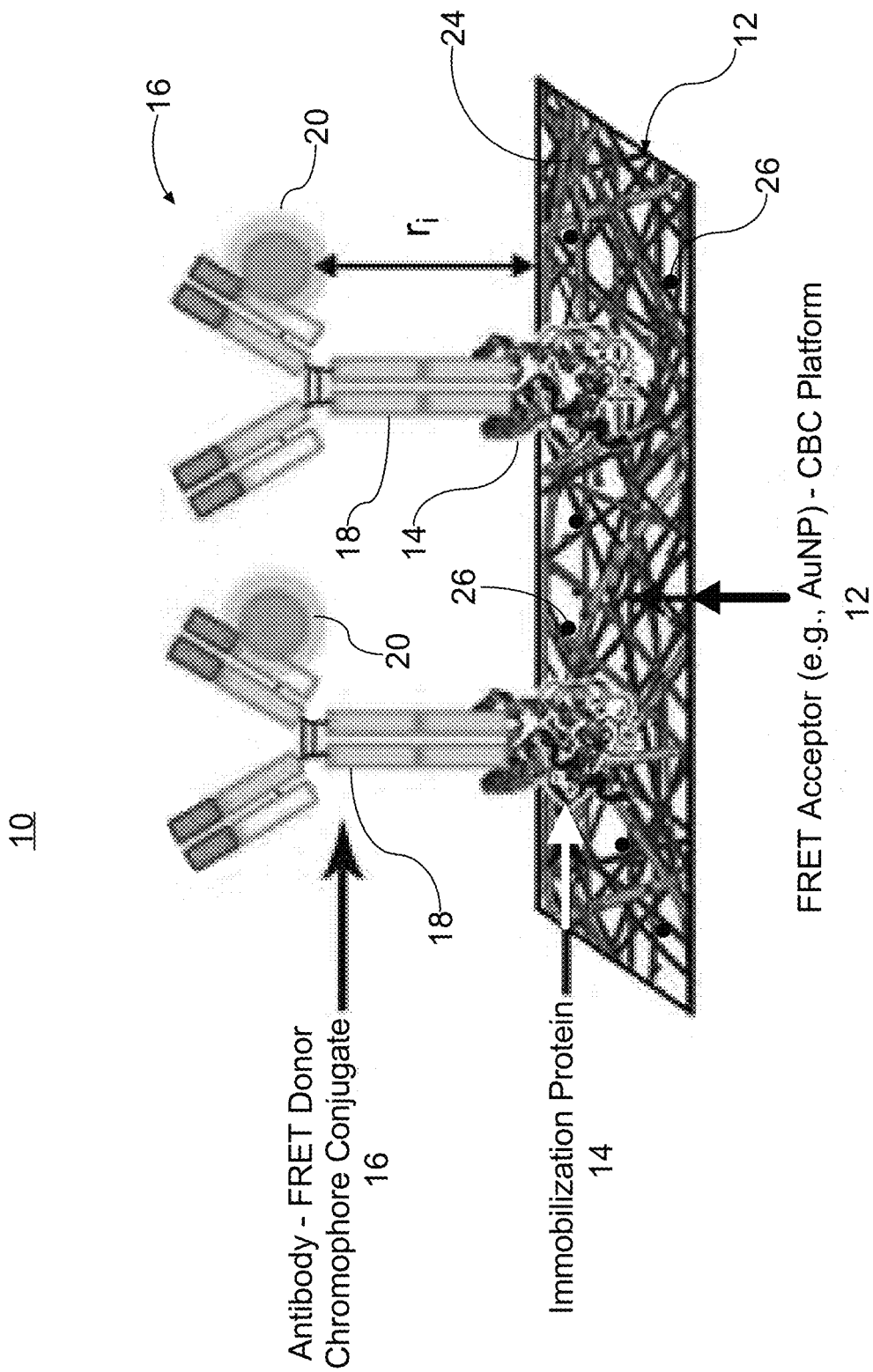
FIG. 1 illustrates an assay device in accordance with an exemplary embodiment of the present invention.

Among the various biosensing approaches and fabricated bioassays, Förster (fluorescence) resonance energy transfer ("FRET") has increasingly emerged as a promising approach, specifically for solution based sensing, due to its sensitivity, selectivity, and rapidness. FRET is a mechanism describing energy transfer from one chromophore (i.e., a donor chromophore) to another chromophore (i.e., an acceptor chromophore). A donor chromophore, initially in an electronic excited state, may transfer energy to an acceptor chromophore through resonance energy transfer (non-radiative dipole-dipole coupling). The efficiency of this energy transfer is inversely proportional to the sixth power of the distance between the donor and acceptor, making FRET sensitive to small changes in distance between the donor and the acceptor chromophores. Fluorescent moieties (fluorophores) can be used as FRET donor chromophores. Both fluorescent moieties (fluorophores) and non-fluorescent moieties (quenchers) can be employed in FRET as acceptor chromophores.

As used herein, the term "FRET chromophore" refers to an acceptor chromophore or a donor chromophore. The term "FRET donor chromophore" (or alternatively "donor chromophore," "FRET donor," or "donor" refers to a FRET chromophore which initially absorbs excitation energy to produce an excited electronic state, and which is then capable of transferring its excitation energy to a nearby FRET acceptor. The term "FRET acceptor chromophore" (or alternatively "acceptor chromophore," "FRET acceptor," or "acceptor") refers to a FRET chromophore to which resonance energy from the donor is subsequently transferred in non-radiative fashion. The energy transfer leads to a reduction in or quenching of the donor's fluorescence intensity and, hence, the term "FRET quencher" or "quencher" may also be used to describe the FRET acceptor moiety of a FRET donor-acceptor pair. In certain embodiments, when the FRET acceptor is a fluorescent moiety, the energy transfer from the FRET donor to the FRET acceptor may also result in an increase in the FRET acceptor's emission intensity. A pair of chromophores that interact in such a manner that FRET occurs may be referred to herein as a "FRET donor-acceptor chromophore pair," "FRET donor-acceptor pair," or "donor-acceptor pair."

In certain embodiments of the present invention, quantum dots are employed as the FRET donor chromophore. In certain embodiments of the present invention, fluorescent chemical compounds are employed as the FRET donor chromophore.

In certain embodiments of the present invention, quantum dots are employed as the FRET donor chromophore and gold nanoparticles are employed as the FRET acceptor chromophore. In certain embodiments of the present invention, fluorescent chemical compounds are employed as the FRET donor chromophore and gold nanoparticles are employed as the FRET acceptor chromophore. Other FRET donor chromophores, FRET acceptor chromophores, and FRET donor-acceptor chromophore pairs are also contemplated.

The Förster distance (R(0)) is defined as the acceptor-donor separation radius for which the transfer rate equals the rate of donor decay (de-excitation) in the absence of acceptor. Thus, when the donor and acceptor radius (r) equals the Förster distance, the transfer efficiency is 50 percent. At this separation radius, 50 percent of the donor excitation energy is transferred to the acceptor via FRET and 50 percent is dissipated through the other available processes (including fluorescence). The Förster distance is therefore the maximum separation between the donor and acceptor FRET chromophores where resonance energy transfer will occur. The Förster distance is typically on the order of nanometers.

To improve FRET-based detection methods for a solid based detection, the present sensor has been integrated into the substrate, such as paper, glass, or other material. In certain embodiments, the present development utilizes bacterial cellulosic materials to address disadvantages of common biosensor substrates, such as lack of flexibility and sustainability. The unique features of bacterial cellulose (BC) (such as crystalline nano-micro fibril structure, high mechanical strength, high porosity, surface area, and optical transparency) in combination with in-situ synthesized noble metal nanoparticles (e.g., gold or silver nanoparticles and others) provides a unique optical sensing approach. It is believed that the bacterial cellulose nanocomposites in accordance with the present disclosure provide a novel substrate for the development of immunoassay through FRET technique. The present inventors are not aware of any report of as-synthesized nanopaper applied in a FRET-based immunosensor.

This approach is a non-radiative energy transfer from a photoexcited fluorophore (donor) to an acceptor molecule with a strong dependency on the distance between these molecules. Among various donor-acceptor pairs, nano-crystal quantum dot and gold nanoparticles are known as being highly efficient ones in the FRET technique. In certain embodiments, nanoscale materials, e.g., with a size less than 100 nm, are employed due to their unique physical and chemical properties such as high surface area and optical and electrical characteristics, which offer myriad opportunities for sensing technology applicable to food packaging.

Figure 2:
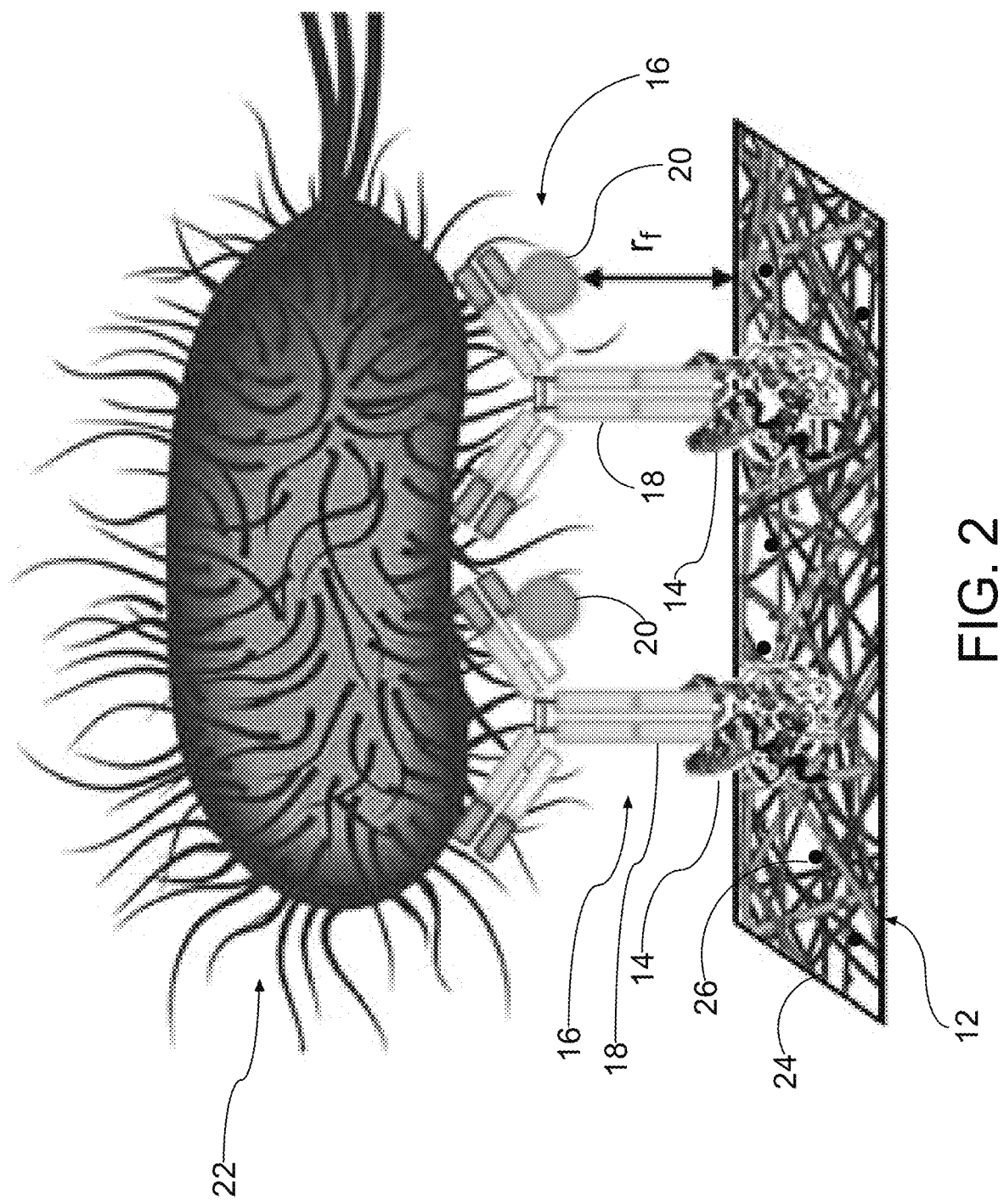
FIG. 2 illustrates the assay device appearing in FIG. 1, wherein a target analyte is bound to an antibody.

Referring to FIGS. 1 and 2, an assay device, designated generally as 10 includes a platform or substrate 12 comprising a nanofiber (i.e., submicron) material 24 impregnated or embedded with nanoparticles 26. The platform 12 may comprise a random or nonwoven mat of a nanofibrous material 24. The mat may be made from short fibers, long discontinuous fibers or continuous fibers. In the preferred embodiments, the platform 12 is formed of bacterial cellulose (BC) as the fibrous material 24 because of its advantageous features and physical properties, such as nanofibrils structure, abundant functional groups, optical transparency, high mechanical strength, and biocompatibility. These characteristics advantageously allow BC to be used as a substrate which can support in-situ synthesis of nanoparticles 26 and conjugation of biomolecules.

Bacterial cellulose is commercially available from Nanonovin Polymer Co. (Mazandaran, Iran) and Axcelon Biopolymers Co. (London, Ontario). Alternatively, bacterial cellulose can be produced by culturing bacteria that produce cellulose, such as *Acetobacter*, *Gluconobacter*, and others. It will be recognized that other fibrous materials are contemplated for use as the solid sensor substrate. In certain embodiments, the platform may comprise a nonwoven mat of submicron polymer fibers, produced, for example, by electrospinning, air blowing, blend spinning, phase separation, and so forth.

In certain embodiments, the hydroxyl groups on the surface BC nanofibers are oxidized to form carboxyl groups to provide more functional groups for the immobilization procedure (described below) while retaining the BC properties. In general, the carboxyl functional groups are created on BC nanofibrils by the TEMPO-oxidation procedure as described by Saito, T. and A. Isogai, "TEMPO-mediated oxidation of native cellulose. The effect of oxidation conditions on chemical and crystal structures of the water-insoluble fractions," *Biomacromolecules*, Vol. 5, No. 5, pp. 1983-1989 (2004), the entire contents of which are incorporated herein by reference.

Example 1

To obtain carboxylated BC (CBC), 250 mg of dried BC was dispersed in 150 mL of MILLI-Q® (ultrapure) water, which contained dissolved TEMPO (7.8 mg) and NaBr (78 mg). To start the oxidation, 11 wt % NaOCl with the ratio of 8:1 (mmol/g BC) was directly added to solution. Immediately, after adequate mixing, the pH was adjusted to 10.5 by adding 0.1 M HCl to trigger oxidation. Since the pH of the solution dropped below 10.5, it was kept constant by adding 0.1 M NaOH due to the dependency of reaction efficiency on the presence of OH$^-$. After an hour of gentle mixing at room temperature, the reaction was stopped by adding ethanol to reach a pH of 7. CBC was separated from the reaction solution and washed sufficiently with ethanol, and then with MILLI-Q® water.

With reference again to FIGS. 1 and 2, the solid surface platform 12 is thus provided with the appropriate features to support the biorecognition and transducer elements of the present development. While not intending to be bound by any particular theory, it is believed that that bacterial cellulose impregnated with gold nanoparticles is particularly advantageous for use in the present system, owing to the plasmonic properties of the gold nanoparticles (which serve as the FRET acceptor) and the abundant carboxyl groups available in the carboxylated bacterial cellulose (CBC).

In certain embodiments, the CBC was impregnated with AuNPs to achieve the acceptor substrate. In the next step, an immobilization protein 14, such as Protein A/G, was covalently immobilized on the nanofiber surface of the AuNP-CBC 12 to keep the antibody in an oriented position. Protein A/G is a recombinant fusion protein that combines IgG binding domains of both Protein A and Protein G. By "immobilized" is meant that the substance capable of holding an analyte is applied in a confined area on the surface of the support such that it is permanently bound or otherwise incapable of substantial movement to positions elsewhere on the support. It will be recognized that other immobilization strategies for immobilizing the antibody on the platform 12 are also contemplated.

In the next step, an antibody-FRET donor chromophore conjugate 16 comprising an antibody 18 linked to a FRET donor chromophore 20 is bonded with the immobilization protein 14 in a well-oriented configuration. The antibody 18 is an antibody that selectively binds with a target analyte 22, such as a bacterium. In certain embodiments, the bacterium is *E. coli*. In certain embodiments, the bacterium is *E. coli* DH-5α. The interaction of the analyte 22 with the antibody-FRET donor chromophore conjugate 16 causes an alteration in the luminescence of the FRET donor chromophore due to the change in distance between the FRET donor chromophore and the acceptor nanopaper as the result of the conformational change induced in the antibody structure after its interaction with the analyte 22.

In reducing the present development to practice, an antibody conjugated to a QD (EAb-QD conjugate) 16 (with emission wavelength of 525 nm) comprising an antibody 18 linked to a quantum dot 20 was bonded with the Protein A/G 14 in a well-oriented configuration. The antibody 18 is an antibody that selectively binds with a target analyte 22, such as a bacterium, e.g., *E. coli* DH-5α. Protein A/G contains four binding domains from Protein A and two from Protein G. Protein A/G can bind strongly to the Fc region of an antibody. Therefore, configuring a well-oriented antibody on the substrate can be obtained by its binding. The interaction of the analyte with the EAb-QD caused an alteration in the luminescence of the QD, due to the change in distance between the QD and the acceptor nanopaper as the result of the conformational change induced in the antibody structure after its interaction with the analyte.

In certain embodiments, the quantum dots utilized as the FRET donor chromophores are carboxyl quantum dots, e.g., QDOT® 525 ITK, which are commercially available from Invitrogen Co. of Carlsbad, Calif. They are made from nanometer scale crystals of a semiconductor material (CdSe), which are shelled with an additional semiconductor layer (ZnS) to improve their chemical and optical properties. This core-shell material is further coated with a polymer layer that allows facile dispersion of the quantum dots in aqueous solutions with retention of their optical properties. The polymer coating has carboxyl groups available for modifications, such as macromolecule attachment.

The conjugation of carboxylated QD to the antibody was performed by a previously described method. See Parolo, C., et al., "Design, Preparation, and Evaluation of a Fixed-Orientation Antibody/Gold-Nanoparticle Conjugate as an Immunosensing Label," *ACS Applied Materials & Interfaces*, Vol. 5, No. 21, pp. 10753-10759 (2013).

Example 2

10 µL of fresh solution of EDC/Sulfo-NHS (composed of 5 mM EDC and 4.6 mM Sulfo-NHS with a ratio of 1:2 (mole/mole)), was mixed with 200 µL of 1.2 nM QD dispersed in MES buffer (freshly prepared 0.01 M MES with pH of 5). After that, the activation of carboxyl groups of the QD was completed by incubating the mixture in the thermos-shaker for 30 min at room temperature and 650 rpm. The excess solution was eliminated through Amicon Ultra-0.5 mL centrifugal filters, cut off 50 kDa for 7 min at 12,000 rpm.

The performance of the present nanopaper-based biosensor was evaluated by using two different antibody and antigen pairs, first anti-HRP (horseradish peroxidase) antibody and HRP, and second, anti-*E. coli* DH-5α antibody and *E. coli* DH-5α bacteria as a representative pathogenic bacteria. The limit of detection of *E. coli* DH-5α using the present biosensor is estimated to be around 10 CFU/mL. The present immunosensor presents a versatile, solid phase, optical-based detector. The present immunosensor was assayed for the recognition of bacteria (*E. coli* DH-5α) and horseradish peroxide (HRP).

The immunosensor utilizes the FRET technique for the detection step, which is a non-radiative energy transfer from a photoexcited donor molecule to an acceptor molecule. The rate of energy transfer highly corresponds to the distance between the donor-acceptor pair since it is less than 20 nm. The efficiency of this energy transfer would be enhanced by maximizing the spectral overlap between the absorbance spectra of acceptor and the emission spectra of the donor. Various nanomaterials may be suite for this technique since they satisfy this criterion. Among varieties of nanoparticles, gold nanoparticles (AuNP) and quantum dots (QD) have been investigated, practically and fundamentally, as a highly efficient pair in FRET technique. However, the critical challenges involved with nanoparticles are their solution-based dispersity as well as their aggregation. The present development overcomes the drawbacks associated with the use of nanoparticles by forming the nanoparticles in situ, as described in greater detail below. Nanoparticles formed of other materials, such as silver nanoparticles, are also contemplated. However, the antibacterial properties of silver nanoparticles may affect the accuracy of the biosensor for bacteria detection and are less preferred.

An exemplary procedure for impregnating the CBC platform with gold nanoparticles is by in situ synthesis in accordance with the Turkevich procedure using $HAuCl_4$ solution as precursor and citric acid trisodium solution as the reducer. See Kimling, J., et al., "Turkevich method for gold nanoparticle synthesis revisited," *The Journal of Physical Chemistry B*, Vol 110, No. 32, pp. 15700-15707 (2006). By synthesizing the nanoparticles in situ, problems associated with nanoparticle aggregation are avoided.

Example 3

In reducing the present development to practice, 15 pieces of CBC (each 1×1 $in^2$) were soaked and mixed in 100 mL of $HAuCl_4$ solution. In order to alter the concentration of fabricated AuNPs, this procedure was carried out individually with various concentrations of precursor solution 0.006 mM, 0.011 mM, 0.023 mM, and 0.045 mM. Once the mixture reached the boiling point, the required citric acid trisodium solution (40 mM) was rapidly added to the container which was 75 µL, 125 µL, 250 µL, and 500 µL, with respect to the precursor concentration. Following 1 hour in the same reaction condition, the gold ions were gradually reduced to AuNPs within the nanofibrils of CBC. The formation of the AuNPs was indicated by the color change of CBC from colorless to light purple. At that moment, the stirring of the mixture was continued without heating to reach room temperature. Then, the synthesized AuNP-CBC pieces were separated from the mixture and washed with plenty of MILLI-Q® water to remove all unreacted Au ions and free AuNPs. The obtained AuNP-CBC pieces were dried at room temperature by keeping them between pieces of filter paper to avoid wrinkles. Through transmission electron microscopy (TEM) images, we observed the spherical AuNPs with an average diameter of about 5.5±1.2 nm.

Taking into account the optical transparency of CBC and plasmonic properties of mono-dispersed AuNP, the in-situ synthesis of AuNP within CBC preserved the plasmonic properties of AuNP whereas the plasmonic spectrum of AuNP-CBC was comparable with mono-dispersed ones. Given these features, AuNP-CBC can perform as the acceptor and quencher. In investigating the effect of the AuNP population density inside of the CBC on accepting the energy transfer from the donor, we found that increasing the AuNP population density enhanced the quenching efficiency of the photoexcited donor.

Figure 3:
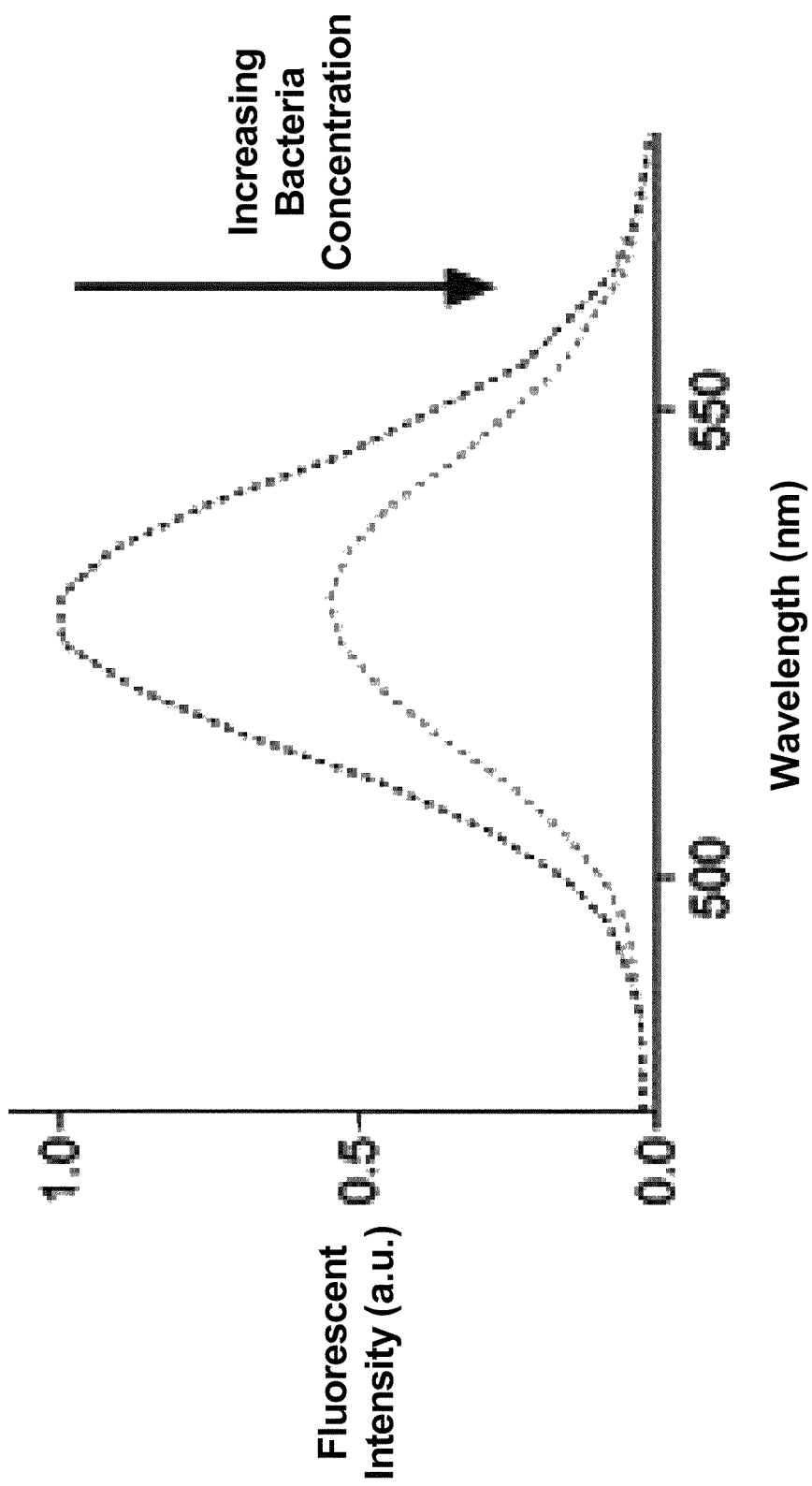
FIG. 3 is a graph of fluorescent intensity, generally illustrating the manner in which quantum dot photoluminescence of the assay device herein decreases as a function of the concentration of the target bacteria in a sample.

FIG. 3 is a graph of fluorescent intensity, showing a decrease in quantum dot photoluminescence upon binding of the *E. coli* DH-5α to the immunosensor prepared by immobilization of antibody against *E. coli* DH-5α conjugated QD (EAb-QD).

Figure 4:
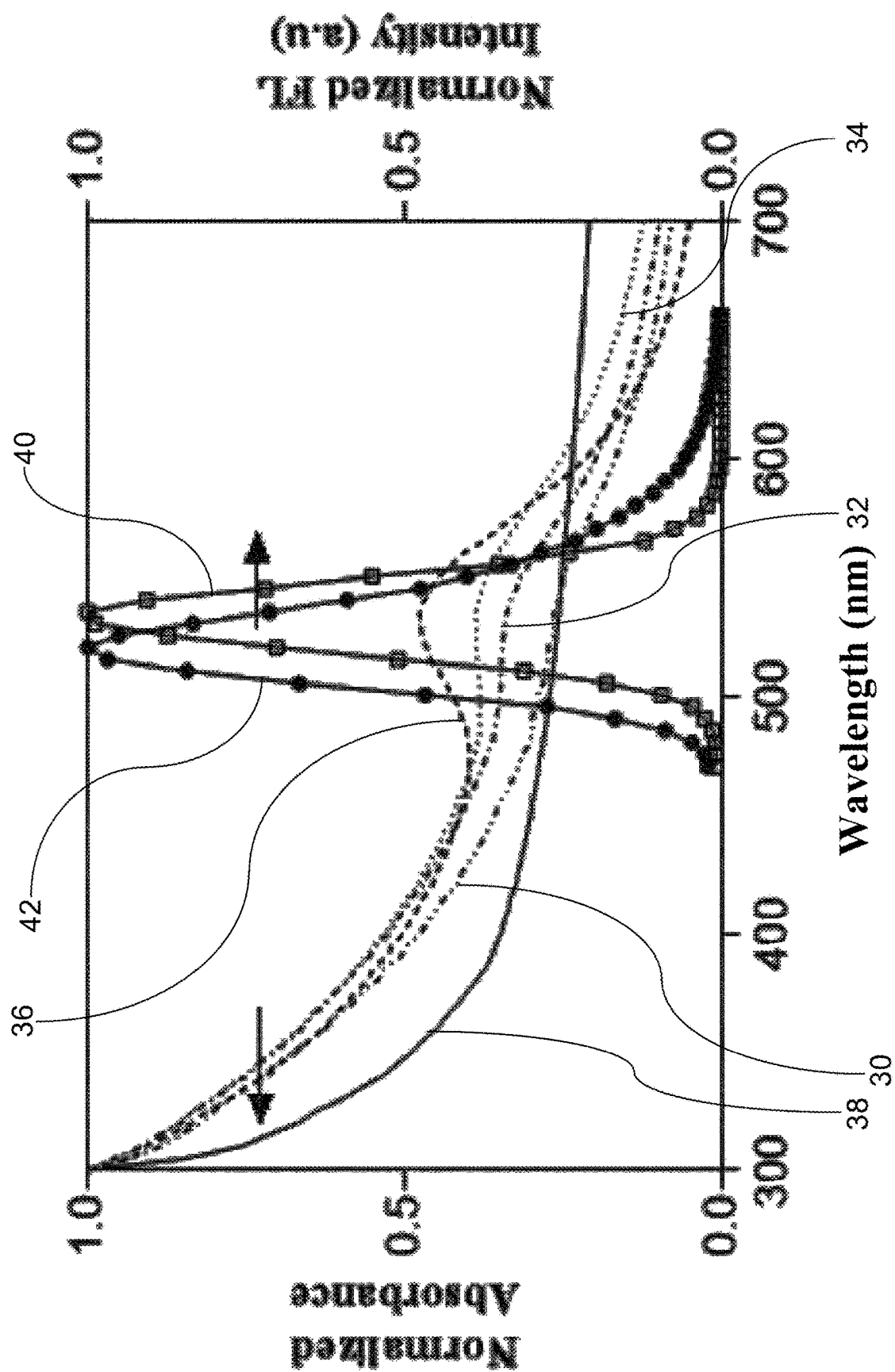
FIG. 4 is a UV-visible absorbance spectra of AuNP-CBC synthesized with different densities of AuNPs.

FIG. 4 is a graph depicting the UV-Vis absorbance spectra for CBC and CBC impregnated with four different densities of AuNPs, as follows:

| | | |
|---|---|---|
| ‐ ‐ ‐ ‐ ‐ | AuNP-CBC (0.006 mM) | (ref. no. 30) |
| ‐ • ‐ • ‐ • | AuNP-CBC (0.011 mM) | (ref. no. 32) |
| •••••••••••• | AuNP-CBC (0.023 mM) | (ref. no. 34) |
| ‐ ‐ ‐ ‐ ‐ ‐ | AuNP-CBC (0.045 mM) | (ref. no. 36) |
| ‐‐‐‐‐‐‐‐‐‐ | CBC | (ref. no. 38) |
| —□— | QD Emission | (ref. no. 40) |
| —●— | ALEXA FLUOR 488 Emission | (ref. no. 42) |

The density of nanoparticles directly influences the plasmonic peak of AuNP-CBCs. FIG. 4 represents an example of AuNP-CBC with four different densities of AuNP, synthesized by using four different concentrations of the precursor, and CBC without AuNP. Once AuNPs are formed, the color of CBC range from colorless to red-violet and pink, with their color intensity being highly dependent on the concentration and the density of AuNPs, as shown in FIG. 4.

While there is no absorbance peak for CBC between 400 to 650 nm, the absorbance spectra of AuNP-CBC reveals a peak at 530 nm, as the result of the plasmon resonance absorption of AuNPs. Upon decreasing the AuNP density within the CBC, the intensity of this plasmonic peak declined and became broader.

Owing to the sensitivity and selectivity, the antibody was exploited as the recognition element by linking on the surface of the substrate (e.g., CBC or AuNP impregnated CBC). Various functional groups on the surface of the antibody facilitate its conjugation to the substrate surface by using appropriate crosslinkers. Here, the antibodies against HRP (anti-HRP) and E. coli DH-5α (anti-E. Coli DH-5α) were conjugated to carboxylated quantum dots through covalent binding between amino groups of the antibodies and carboxyl groups of the quantum dots through EDC/Sulfo-NHS chemistry. The QD serves as the donor molecule here.

Regarding the "Y" shape of the antibody, its two active sites are free to attach to the antigen when the antibody is located on the surface from its tail. To achieve the highly efficient structure, antibodies conjugated to QD were linked on the surface of AuNP-CBC platform through affinity binding between Protein A/G and the antibody. This strategy allows controlling the appropriate orientation of the bonded antibody although other immobilization strategies are contemplated.

The Protein A/G is immobilized on the surface of the platform through covalent binding between its amino groups and carboxyl groups of AuNP-CBC. The carboxylated bacterial cellulose impregnated with AuNP is implemented as the solid platform to support the biorecognition elements protein A/G and EAb-QD. Upon recognition of bacteria by the immunosensor there is a conformational change in the three dimensional structure of the EAb-QD that leads to the decrease of QD photoluminescence. This phenomenon is due to the reduction of the effective distance between the donor (QD) and the acceptor (AuNP-CBC) from $r_i$ (see FIG. 1) to $r_f$ (see FIG. 2).

Example 4

In reducing the present development to practice, the Protein A/G was covalently immobilized on the surface of CBC and AuNP-CBC through EDC/Sulfo-NHS chemistry. The activated carboxyl groups on the surface of the nanofibrils were bound to the primary amines of the Protein A/G.

It should be noted that in the description below, MES and PBS buffers refer to the freshly prepared 0.01 M MES and PBS with pH of 5 and 7.4, respectively, unless stated otherwise. The immobilization procedure was as follows: EDC and Sulfo-NHS solution were freshly prepared by dissolving in MES buffer. The respective nanopapers were cut in circular shape of 6 mm and placed in a 96 well microplate. Then, the nanopapers platforms were sequentially washed with water, PBS and MES buffer (each step was done for 20 min at room temperature and 650 rpm). Then, 40 µL of the fresh mixture of EDC and Sulfo-NHS, composed of 5 mM EDC and 4.6 mM Sulfo-NHS with a ratio of 1:2 (mole/mole), was added to the nanopaper platforms. The activation of CBC was completed in 20 min by incubation in a thermo-shaker at room temperature and 650 rpm.

In certain embodiments, the presence of a target analyte in a sample is optically detectable based on a change in signal of the FRET donor-acceptor chromophore pair, and the absence of a target analyte in a sample is optically detectable based on a lack of a change in signal of the FRET donor-acceptor chromophore pair. In certain embodiments, the change in signal is a decrease in signal, e.g., a decrease in fluorescence emission intensity of the FRET donor chromophore of a FRET donor-acceptor chromophore pair. In alternative embodiments, the change in signal is an increase in signal, e.g., in the case of a fluorophore employed as the FRET acceptor, an increase in fluorescence emission intensity of the FRET acceptor chromophore of a FRET donor-acceptor chromophore pair.

The FRET is triggered after capturing the antigen (either HRP or E. coli DH-5α) by the immobilized antibody-QD, which leads to the reduction of QD luminescence. The reduction is due to the decrease in the distance between the donor (QD) and the acceptor (AuNP-CBC) as the result of the conformational change in the 3D structure of antibody after interacting with antigen. The quenching efficiency of QD corresponded to the concentration of bacteria as by increasing the concentration of bacteria ($10^8$ and 10 CFU/mL) the fluorescent intensity of QD decreased.

Figure 5:
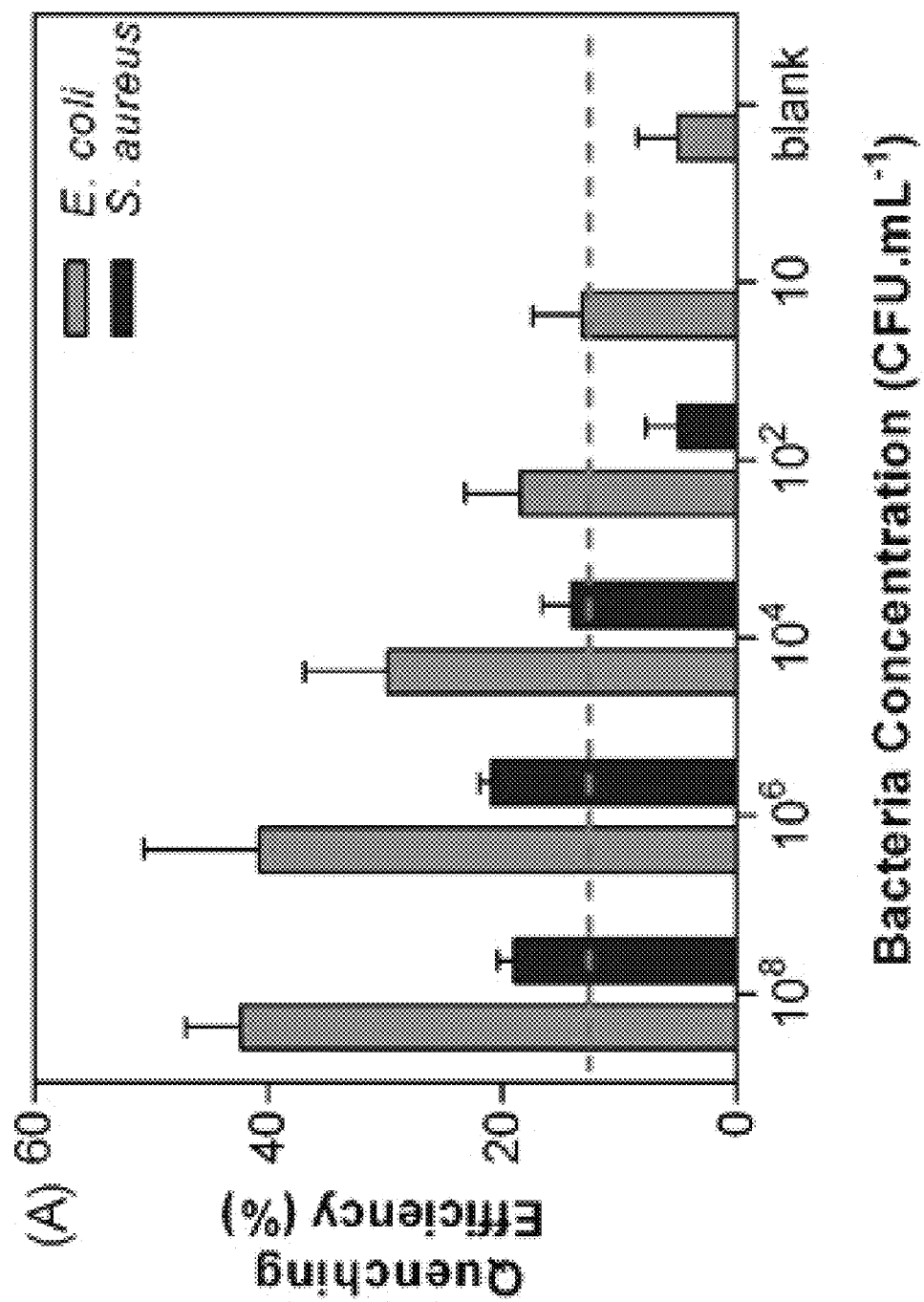
FIG. 5 is a graph of quenching efficiency vs. bacteria concentration when detecting *Staphylococcus aureus* (*S. aureus*) to evaluate immunosensor specificity/selectivity against a gram-positive bacteria. The graph appearing in FIG. 5 compares immunosensor functionality in accordance with this disclosure prepared by immobilization of antibody against *E. coli* DH-5α conjugated QD (EAb-QD).
Figure 6:
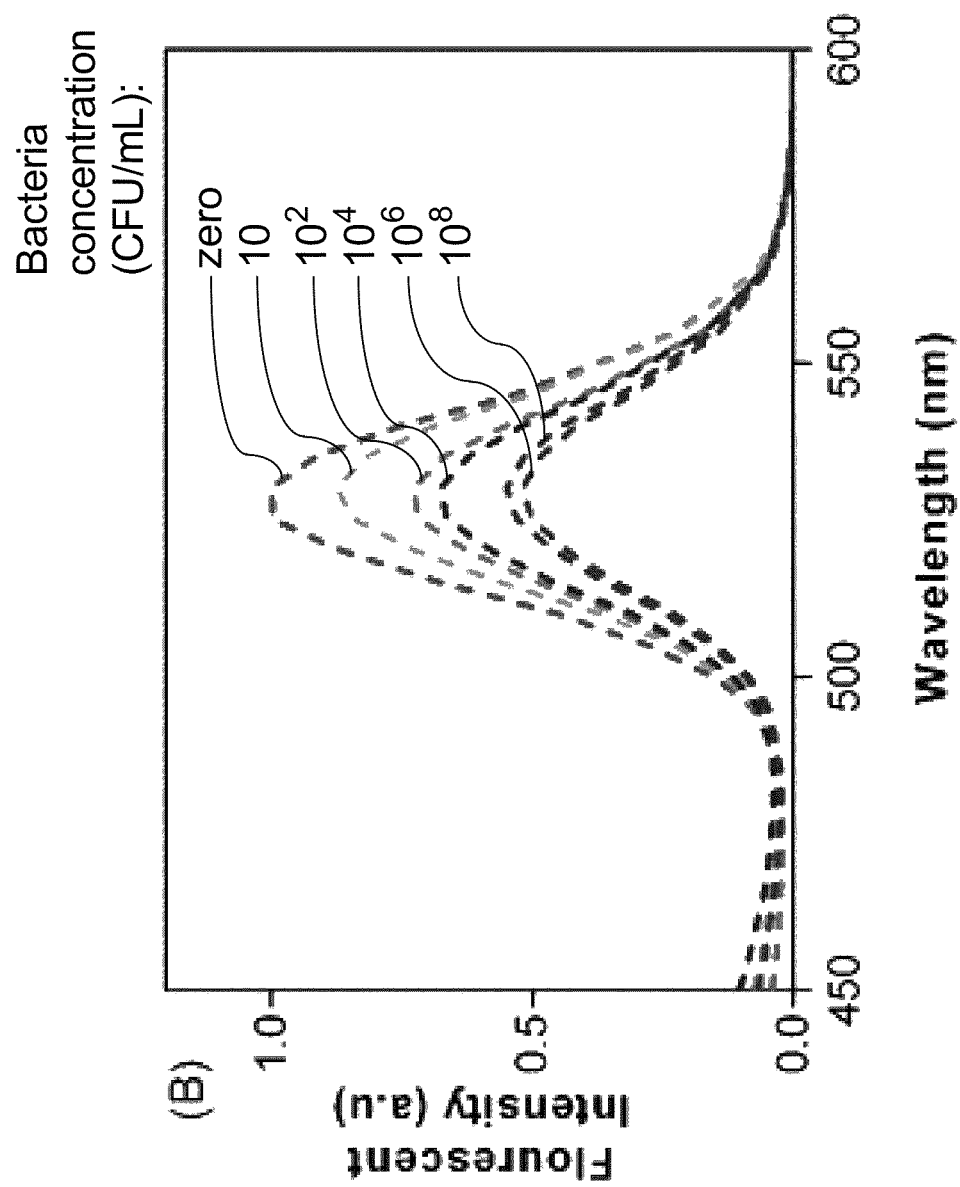
FIG. 6 is a graph of fluorescent intensity vs. wavelength after recognition of *coli* DH-5α, showing a decrease in quantum dot photoluminescence upon binding of the *E. coli* DH-5α to the immunosensor prepared by immobilization of antibody against *E. coli* DH-5α conjugated QD (EAb-QD).

FIGS. 5 and 6 illustrate the quenching efficiency and fluorescent intensity, respectively, of QD after the recognition of E. coli DH-5α. The limit of detection (LOD) threshold was determined to be as low as 10 CFU/mL, confirming the sensitivity of the present nanopaper and FRET-based immunosensor. FIG. 5 illustrates the selectivity of the immunosensor employing EAb-QD by comparing quenching efficiency as a function of bacteria concentration for both a target analyte (E. coli DH-5α, represented by the grey bars) and a control bacteria (here, the gram positive bacteria S. aureus, represented by the black bars). FIG. 6 illustrates the change in fluorescent intensity of QD after its response to E. coli DH-5α detection at various concentrations of bacteria.

To evaluate the specificity and selectivity of the developed FRET-based immunosensor, Staphylococcus aureus (S. aureus) was selected as a control bacteria. The estimated quenching efficiency for the highest concentration of S. aureus ($10^8$ and $10^6$ CFU/mL) was within the range of the calculated LOD for E. coli DH-5α. Meanwhile, by decreasing the concentration of S. aureus (from $10^4$ to $10^2$ CFU/mL), the respective quenching efficiencies declined under the LOD threshold. Despite the limited interaction of the immunosensor with the control bacteria, it can be employed for sensitive E. coli DH-5α recognition.

The performance of the immunosensor for detecting HRP (the selected concentration saturated the antibodies active site) was estimated by quenching efficiency of QD around 30%. So, by comparing the results of immunosensor performance for two different antigens, it can be suggested that the proposed immunosensor is more efficient for detecting large antigens such as bacteria.

The present inventors have studied the inherent feature of antibody for the varieties of antibody-antigen interaction, which has revealed that the interaction of an antibody with a big antigen such as bacteria caused a severe conformational change in its structure in comparison with a small antigen, such as horseradish peroxidase. Thus, the quenching efficiency of QD evaluated after the interaction of HRP and *E. coli* DH-5α with immunosensor may confirm the previous fundamental investigation. As the interaction of the immunosensor with the bacteria resulted in a significant change in the structure of the antibody, the higher quenching efficiency was evaluated. Thus, the sensed output is advantageously based on an intrinsic characteristic (conformational change) of the antibody itself.

It will be recognized that other FRET donor chromophores, such as fluorescent dye fluorophores, may be used in place of the semiconductor quantum dot donors.

Example 5

To examine the effect of alternative FRET donor chromophores, a fluorescent dye, ALEXA FLUOR® 488 (available from Molecular Probes, Inc. of Eugen, Oreg.), was selected. ALEXA FLUOR possesses high brightness, photostability, and pH insensitivity in compare with the other types of fluorescent dye. Besides, the emission spectra band of ALEXA FLUOR 488 (having an emission wavelength of 520 nm when exited at 488 nm) has acceptable overlap with the absorbance spectra of AuNP-CBC (carboxylated bacterial cellulose impregnated with gold nanoparticle), as described above. FIG. 4 illustrates the emission spectra of ALEXA FLUOR and its overlap with the absorbance spectra of AuNP-CBC.

Ready-to-use polyclonal antibody produced in a rabbit against *E. coli* DH-5α conjugated to ALEXA FLUOR 488 (EAb-AF) was purchased from Bioss Inc. of Woburn, Mass. The platform preparation, including synthesizing the AuNP-CBC, the conjugation of protein A/G or protein A (PA) and the immobilization of antibody) proceeded as described above.

Figure 7:
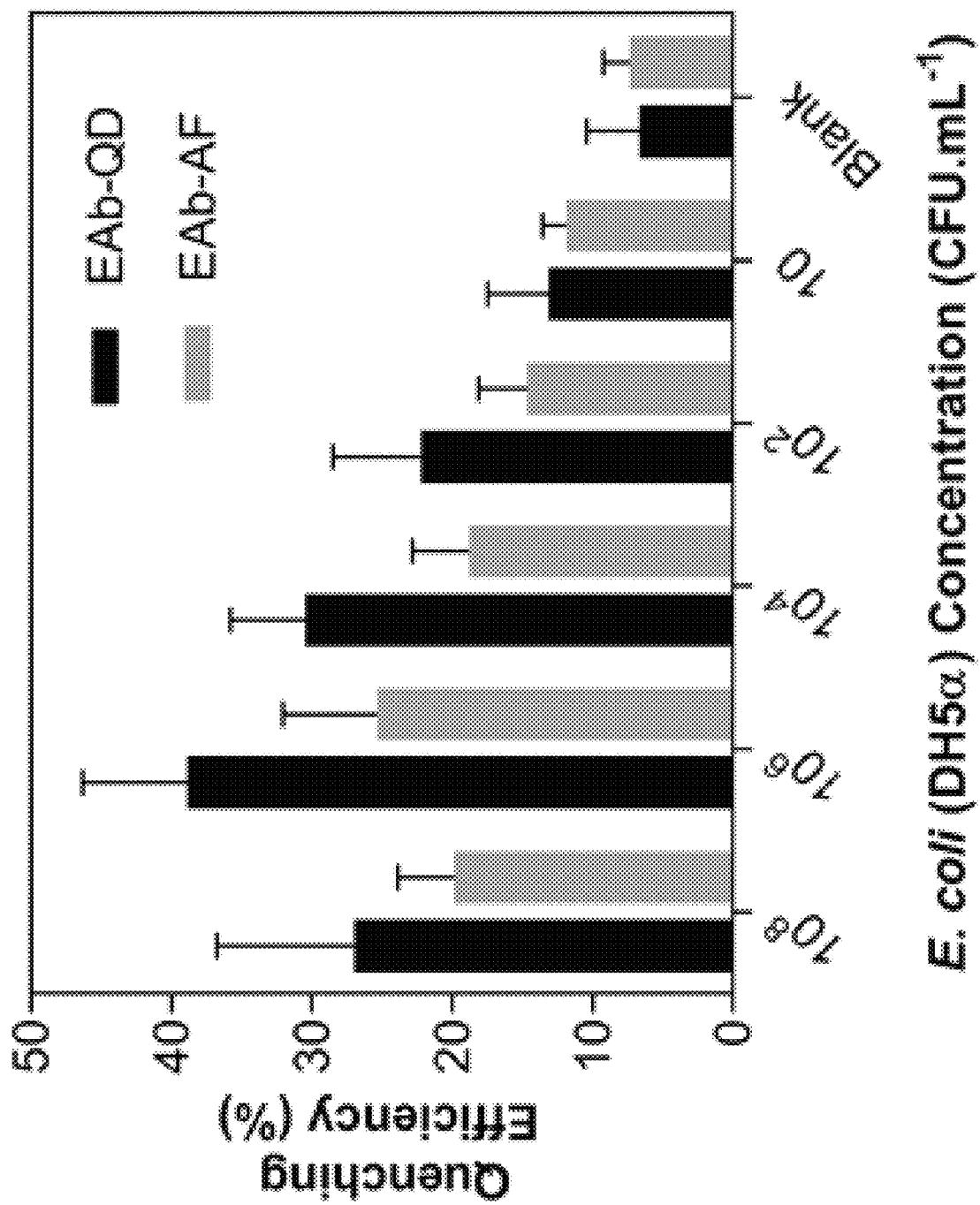
FIG. 7 is a graph of quenching efficiency vs. *E. coli* DH-5α bacteria concentration to compare the functionality of immunosensors employing fluorescent dye FRET donors and immunosensors employing quantum dot FRET donors. The graph in FIG. 7 compares immunosensors in accordance with this disclosure prepared by immobilization of the antibody against *E. coli* DH-5α conjugated with ALEXA FLUOR® 488 (EAb-AF) with immunosensors in accordance with this disclosure prepared by the immobilization of the antibody against *E. coli* DH-5α conjugated with quantum dots (EAb-QD).

The prepared immunosensor (AuNP-CBC-PA/EAb-AF) was then examined to detect *E. coli* DH-5α with the concentrations of $10^8$ to $10^1$ CFU/mL dispersed in standard buffer (10 mM PBS, pH 7.4). FIG. 7 compares the results of bacteria detection through immunosensors prepared by the antibody against *E. coli* DH-5α conjugated with ALEXA FLUOR (EAb-AF) or quantum dot (EAb-QD). As a result, although the immunosensor integrated with EAb-AF can reveal the presence of bacteria, the value of quenching efficiency is less than of the immunosensor with EAb-QD. The limit of detection (LOD) for both types of immunosensors is estimated to be around 50 CFU/mL, wherein the limit of detection for each system was determined through the mean of the blank solution quenching efficiency plus three times that of its standard deviation. This result demonstrates that the present design of immunosensor is trustworthy.

Example 6

The specificity or selectivity of the immunosensor in accordance with this disclosure was evaluated by using antibodies against a first strain of *E. coli* to prepare the immobilized antibody-FRET donor chromophore conjugate and using a second, similar strain of *E. coli* as the target analyte. In this Example, the target analyte was *E. coli* (ATCC 25922) ($10^6$ to 10 CFU/mL) immunosensors in accordance with this disclosure prepared by immobilization of the antibody against *E. coli* DH-5α conjugated with ALEXA FLUOR 488 (EAb-AF) with immunosensors in accordance with this disclosure prepared by the immobilization of the antibody against *E. coli* DH-5α conjugated with quantum dots (EAb-QD).

Figure 8:
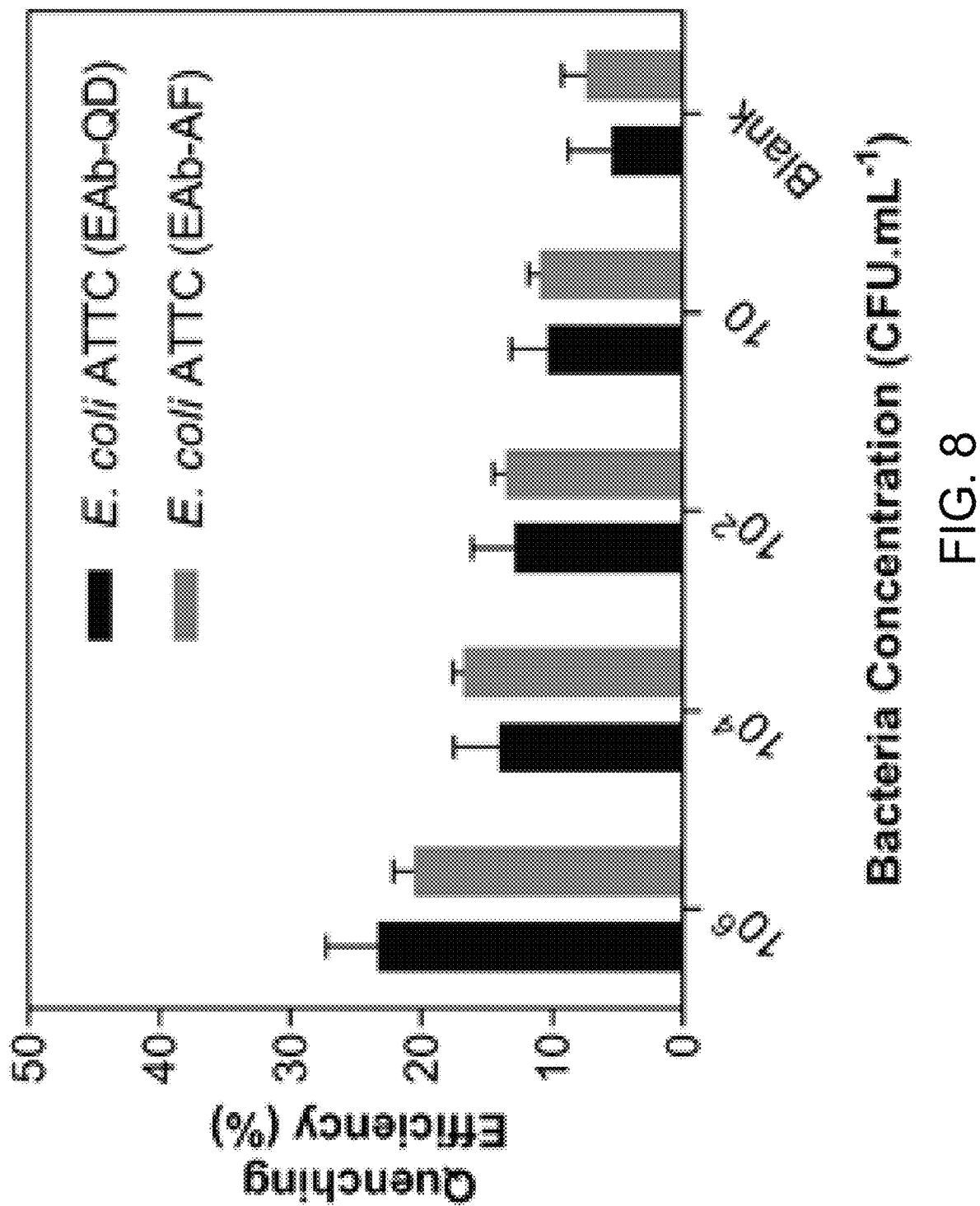
FIG. 8 is a graph of quenching efficiency vs. bacteria concentration when detecting a similar strain of *E. coli*, such as *E. coli* ATCC 25922 to evaluate immunosensor specificity/selectivity. The graph appearing in FIG. 8 compares immunosensors in accordance with this disclosure prepared by immobilization of the antibody against *E. coli* DH-5α conjugated with ALEXA FLUOR 488 (EAb-AF) with immunosensors in accordance with this disclosure prepared by the immobilization of the antibody against *E. coli* DH-5α conjugated with quantum dots (EAb-QD).

To evaluate the specificity of the developed immunosensors, another strain of *E. coli*, ATCC 25922, was selected. The various concentrations of *E. coli* (ATCC 25922) ranged from $10^6$ to 10 CFU/mL, which were allocated to the prepared immunosensors as described above, namely, AuNP-CBC-PA/EAb-QD and AuNP-CBC-PA/EAb-AF. As FIG. 8 shows, for the high concentrations of *E. coli* (ATCC 25922) i.e., $10^6$ to $10^4$ CFU/mL, there is a partial detection. This reveals a slight cross-reactivity of the immunosensors due to the interaction of the applied anti-*E. coli* DH-5α antibody with *E. coli* (ATCC 25922). This may result from the presence of similar epitopes on the cell of *E. coli* bacteria that are responsible for attaching to the antibody. Here, the use of polyclonal antibody may have highlighted this cross-reactivity. The use of a monoclonal antibody of a specific strain may provide increased selectivity and specificity.

Example 7 evaluates the functionality of the immunosensor in accordance with this disclosure against the bacteria when dispersed in the matrix of a real sample.

Example 7

To evaluate the functionality of the immunosensors in accordance with this disclosure against bacteria dispersed in the matrix of a real sample, a poultry (chicken) extract and lettuce juice were used. The chicken extract was obtained directly from the chicken breast muscle freshly obtained from a butcher shop. The lettuce juice was prepared from green leaves of lettuce freshly obtained from a grocery store. To prepare the chicken extract, 50 grams of the chicken were mixed completely with 250 mL of PBS buffer in a smoothie maker device. To prepare the lettuce juice, 50 grams of the lettuce leaves were mixed completely with 250 mL of PBS buffer in a smoothie maker device. Afterward, each of the obtained homogenates were respectively filtered with WHATMAN® filter paper No. 1 (Whatman International Limited, Kent, England) to eliminate all suspended residues. Then, the various concentrations of bacteria suspension were prepared by diluting the stock solution with the resulted filtrates.

The evaluation of *E. coli* (DH5α) detection with the concentrations of $10^6$, $10^4$, $10^2$ and 10 CFU/mL for platforms fabricated with (1) AuNP-CBC-PA with immobilized EAb-QD and (2) AuNP-CBC-PA with immobilized with EAb-AF were conducted as previously performed for bacteria detection in the standard buffer.

Figure 9:
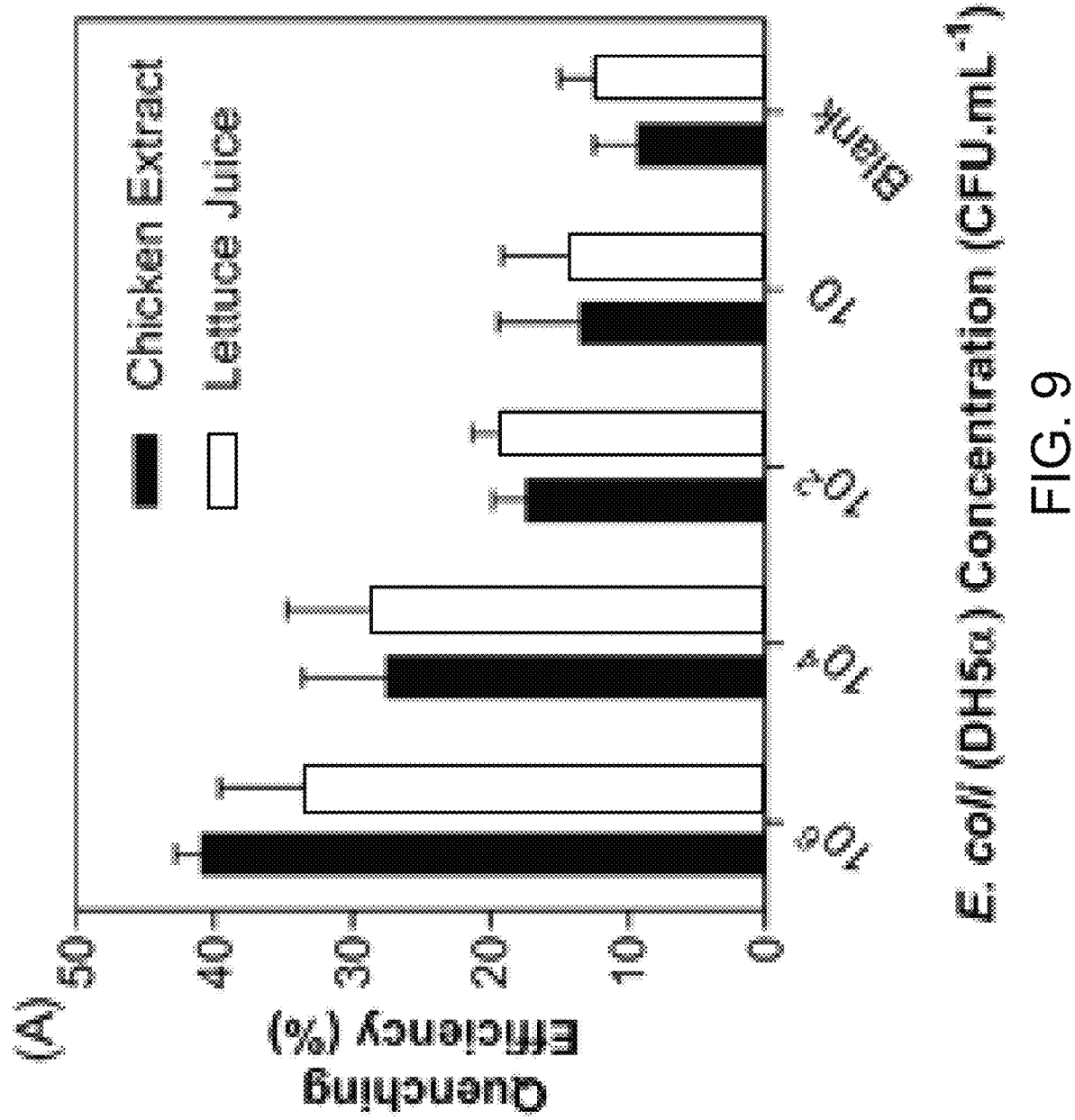
FIG. 9 is a graph of quenching efficiency vs. bacteria concentration depicting the performance of the EAb-QD immunosensors in accordance with this disclosure in detecting bacteria in the matrix of real samples comprising chicken extract and lettuce juice.
Figure 10:
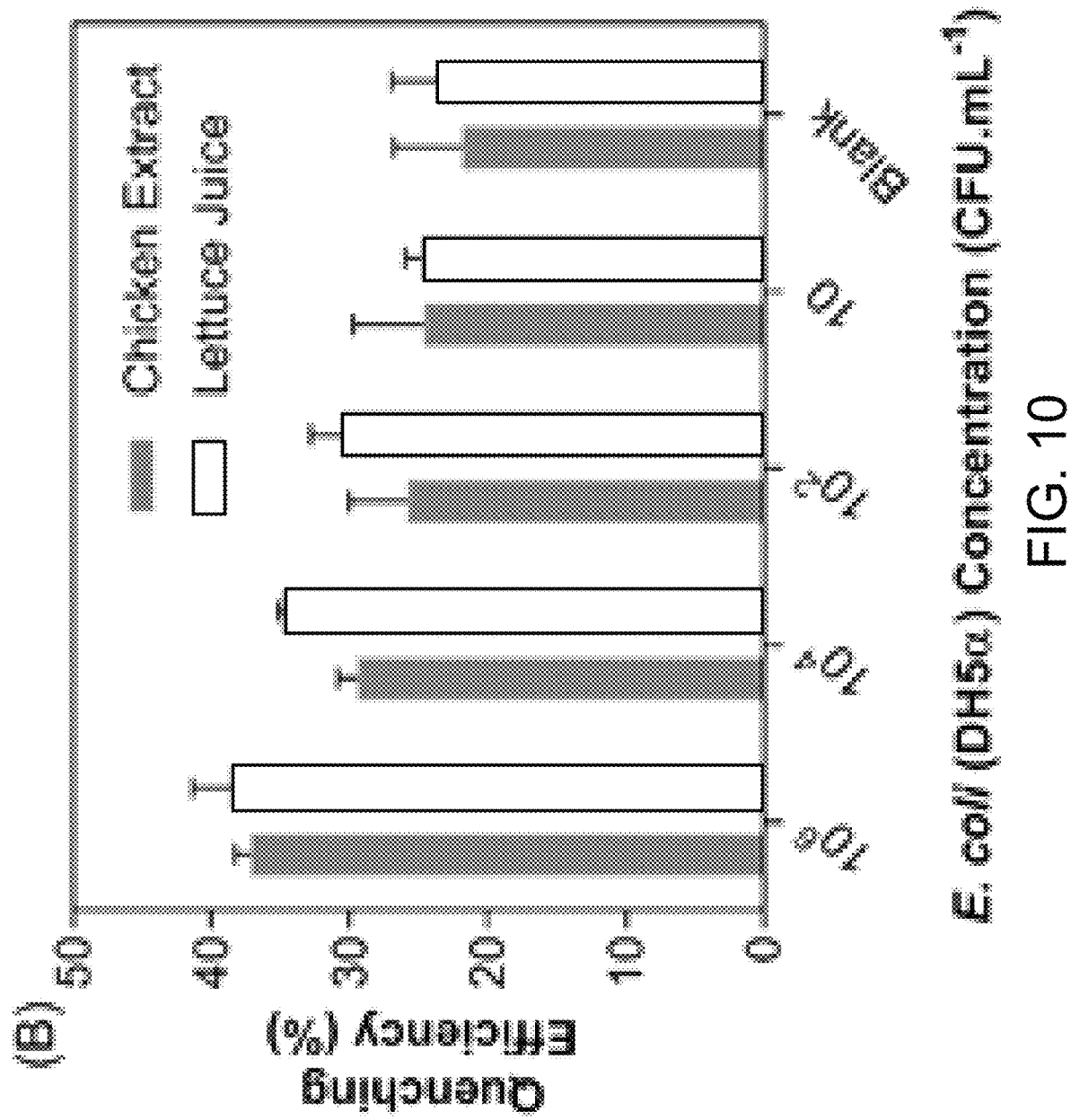
FIG. 10 is a graph of quenching efficiency vs. bacteria concentration depicting the performance of the EAb-AF immunosensors in accordance with this disclosure in detecting bacteria in the matrix of real samples comprising chicken extract and lettuce juice.

FIGS. 9 and 10 illustrate the performance of each immunosensor platform to detect the suspended bacteria in the chicken extract and lettuce juice matrices, respectively. By their comparison, the immunosensor fabricated with EAb-QD exhibited a higher performance for the detection of bacteria. The estimated threshold of LOD for the immunosensor decorated with EAb-QD in both the chicken extract and lettuce juice matrices was approximately ~$10^2$ CFU/mL. The immunosensor with EAb-AF showed poorer performance with a LOD of $10^4$ CFU/mL for the chicken extract and $10^6$ CFU/mL for the lettuce juice. This limit of detection is not enough to be labeled as a sensitive sensor.

In certain embodiments, packaging materials and packaging articles formed of the same employing the present immunosensor are provided. A packaging article, including food packaging and others, may be formed of a sheet material, which may be formed of paper, metal foils (e.g., aluminum foil), plastic polymers, and laminates and coextrusions thereof. Exemplary plastic polymers include polyolefins such as polyethylene (PE), low density polyethylene (LDPE), high density polyethylene (HDPE), linear low density polyethylene (LLDPE), polypropylene (PP), polyesters such as polyethylene terephthalate (PET), polyvinyl chloride (PVC), polyvinylidene chloride (PVDC), polystyrene (PS), ethyl vinyl alcohol (EVOH), and so forth.

The biosensor in accordance with this disclosure is incorporated into the packaging material on an interior surface thereof wherein it will come into contact with a food product or other sample to be packaged. In certain embodiments, for samples containing liquid, the biosensor is incorporated on an interior surface of thereof wherein it will come into direct contact with the liquid. Alternatively, in certain embodiments for samples containing liquid, the food product may be separated from direct contact with the biosensor via a porous or fibrous membrane through which liquids may readily pass through, provided that the porous or fibrous membrane has openings or pore sizes that do not prevent the target analyte, such as a target bacteria, from passing through the membrane and interacting with the surface of the biosensor.

An exemplary packaging article 30 employing the biosensor herein appears in FIG. 11. The packaging article 30 is formed of a sheet material 32 and includes an assay device 10 on an interior surface thereof. The illustrated location is exemplary only and it will be recognized that the location of the biosensor should be selected such that it will come into contact with the packaging contents under certain conditions. In certain embodiments, the packaging article is formed of a sheet material which is transparent, or at least transparent in the region where the assay device 10 is located to allow optical detection of the device 10 through the packaging without opening the package. In the case of opaque packaging materials, it is contemplated that optical detection of the device 10 may occur after opening the packaging and prior to consumption of the product.

In certain embodiments, the use of a handheld computing device such as an optical scanner or mobile telephone device, such as a smart phone equipped with a camera, is contemplated for use as a substitute for expensive and nonportable analytical devices. Smart phones, with a camera, computer processor, and operating system allow the use of smartphones as a biosensor accessory wherein the smartphone camera serves as the optical sensor for optical detection based on absorbance, reflectance, fluorescence, surface plasmon resonance (SPR), bio-chemiluminescence, electrochemiluminescence, and so forth. In certain embodiments, the smart phones or other handheld computing devices can be equipped with special lenses or filters to produce fluorescence images.

The invention has been described with reference to the preferred embodiment. Modifications and alterations will occur to others upon a reading and understanding of the preceding detailed description. It is intended that the invention be construed as including all such modifications and alterations insofar as they come within the scope of the appended claims or the equivalents thereof.

CITED REFERENCES

All references cited herein are incorporated herein by reference in their entireties.

1. Lund, B. M.; O'Brien, S. J., The occurrence and prevention of foodborne disease in vulnerable people. *Foodborne Pathogens and Disease* 2011, 8(9), 961-973.
2. Scallan, E.; Hoekstra, R. M.; Angulo, F. J.; Taupe, R. V.; Widdowson, M.-A.; Roy, S. L; Jones, J. L.; Griffin, P. M., Foodborne illness acquired in the United States—major pathogens. *Emerg Infect Dis* 2011, 17(1) 7-15.
3. Zhao, X.; Lin, C.-W.; Wang, J.; Oh, D. H., Advances in rapid detection methods for foodborne pathogens. *J. Microbiol. Biotechnol.* 2014, 24(3), 297-312.
4. Lazcka, O.; Del Campo, F. J.; Muñoz, F. X., Pathogen detection: a perspective of traditional methods and biosensors. *Biosensors and Bioelectronics* 2007, 22(7), 1205-1217.
5. Kagan, C. R., At the Nexus of Food Security and Safety: Opportunities for Nanoscience and Nanotechnology. *ACS Nano* 2016, 10(3), 2985-2986.
6. Chen, J.; Andler, S. M.; Goddard, J. M.; Nugen, S. R.; Rotello, V. M., Integrating recognition elements with nanomaterials for bacteria sensing. *Chemical Society Reviews* 2017, 46(5), 1272-1283.
7. Sutarlie, L.; Ow, S. Y.; Su, X., Nanomaterials-based biosensors for detection of microorganisms and microbial toxins. *Biotechnology Journal* 2016 12(4).
8. Vikesland, P. J.; Wigginton, K. R., Nanomaterial enabled biosensors for pathogen monitoring—a review. *Environmental Science & Technology* 2010, 44(10), 3656-3669.
9. Ray, P. C.; Fan, Z.; Crouch, R. A.; Sinha, S. S.; Pramanik, A., Nanoscopic optical rulers beyond the FRET distance limit: fundamentals and applications. *Chemical Society Reviews* 2014, 43(17), 6370-6404.
10. Jin, B.; Wang, S.; Lin, M.; Jin, Y.; Zhang, S.; Cul, X.; Gong, Y.; Li, A.; Xu, F.; Lu, T. J., Upconversion nanoparticles based FRET aptasensor for rapid and ultrasensitive bacteria detection. *Biosensors and Bioelectronics* 2017, 90, 525-533.
11. Morales-Narváez, E.; Hassan, A. R.; Merkoçi, A., Graphene oxide as a pathogen-revealing agent sensing with a digital-like response. *Angewandte Chemie* 2013, 125(51), 14024-14028.
12. Ko, S.; Grant, S. A., A novel FRET-based optical fiber biosensor for rapid detection of *Salmonella typhimurium*. *Biosensors and Bioelectronics* 2006, 21(7), 1283-1290.
13. Chen, G.; Song, F.; Xiong, X.; Peng, X., Fluorescent nanosensors based on fluorescence resonance energy transfer (FRET). *Industrial & Engineering Chemistry Research* 2013, 52(33), 11228-11245.
14. Hötzer, B.; Medintz, I. L; Hildebrandt, N., Fluorescence in nanobiotechnology: sophisticated fluorophores for novel applications. *Small* 2012, 8(15), 2297-2326.
15. Resch-Genger, U.; Grabolle, M.; Cavaliere-Jaricot, S.; Nitschke, R.; Nann, T., Quantum dots versus organic dyes as fluorescent labels. *Nature Methods* 2008, 5(9), 763-775.
16. Pons, T.; Medintz, I. L.; Sapsford, K. E.; Higashiya, S.; Grimes, A. F.; English, D. S.; Mattoussi, H., On the quenching of semiconductor quantum dot photoluminescence by proximal gold nanoparticles. *Nano Letters* 2007, 7 (10), 3157-3164.
17. Hildebrandt, N.; Spillmann, C. M.; Alger, W. R.; Pons, T.; Stewart, M. H.; Oh, E.; Susumu, K.; Diaz, S. A.; Delehanty, J. B.; Medintz, I. L., Energy transfer with semiconductor quantum dot bioconjugates: a versatile platform for biosensing, energy harvesting, and other developing applications. *Chemical Reviews* 2017, 117 (2), 536-711.

18. Morales-Narváez, E.; Golmohammadi, H.; Naghdi, T.; Yousetl, H.; Kostiv, U.; Horák, D.; Pourreza, N.; Merkoçi, A., Nanopaper as an optical sensing platform. *ACS Nano* 2015, 9 (7), 7296-7305.
19. Heli, B.; Morales-Narváez, E.; Golmohammadi, H.; Ajji, A.; Merkoçi, A., Modulation of population density and size of silver nanoparticles embedded in bacterial cellulose via ammonia exposure: visual detection of volatile compounds in a piece of plasmonic nanopaper. *Nanoscale* 2016, 8(15), 7984-7991.
20. Pourreza, N.; Golmohammadi, H.; Naghdi, T.; Yousefi, H., Green in-situ synthesized silver nanoparticles embedded in bacterial cellulose nanopaper as a bionanocomposite plasmonic sensor. *Biosensors and Bioelectronics* 2015, 74, 353-359.
21. Heli, B.; Ajji, A., Nanopaper-based platform applicable in solid-state based FRET technique. *Biochimica et Biophysica Acta* 2017, submitted
22. Sela-Culang, I.; Alon, S.; Ofran, Y., A systematic comparison of free and bound antibodies reveals binding-related conformational changes. *The Journal of Immunology* 2012, 189(10), 4890-4899.
23. Elgert, K. D., *Immunology: Understanding the Immune System*. John Wiley & Sons: 2009.
24. Saito, T.; Isogai, A., TEMPO-mediated oxidation of native cellulose. The effect of oxidation conditions on chemical and crystal structures of the water-insoluble fractions. *Biomacromolecules* 2004, 5(5), 1983-1989.
25. Da Silva Perez, D.; Montanari, S.; Vignon, M. R., TEMPO-mediated oxidation of cellulose III. *Biomacromolecules* 2003, 4(5), 1417-1425.
26. Kimling, J.; Maier, M.; Okenve, B.; Kotaidis, V.; Ballot, H.; Plech, A., Turkevich method for gold nanoparticle synthesis revisited. *The Journal of Physical Chemistry B* 2006, 110(32), 15700-15707.
27. Parolo, C.; de la Escosura-Muñiz, A.; Polo, E.; Grazó, V.; de la Fuente, J. M.; Merkoçi, A., Design, preparation, and evaluation of a fixed-orientation antibody/gold-nanoparticle conjugate as an immunosensing label. *ACS Applied Materials & Interfaces* 2013, 5(21), 10753-10759.
28. Iguchi, M.; Yamanaka, S.; Budhiono, A., Bacterial cellulose—a masterpiece of nature's arts. *Journal of Materials Science* 2000, 35(2), 261-270.
29. Yamanaka, S.; Watanabe, K; Kitamura, N.; Iguchi, M.; Mitsuhashi, S.; Nishi, Y.; Uryu, M., The structure and mechanical properties of sheets prepared from bacterial cellulose. *Journal of Materials Science* 1989, 24(9), 3141-3145.
30. Kim, H.; Kang, D.-Y.; Goh, H.-J.; Oh, B.-K.; Singh, R. P.; Oh, S.-M.; Choi, J.-W., Analysis of direct immobilized recombinant protein G on a gold surface. *Ultramicroscopy* 2008, 108(10), 1152-1156.
31. Makaraviciute, A.; Ramanaviciene, A., Site-directed antibody immobilization techniques for immunosensors. *Biosensors and Bioelectronics* 2013, 50, 460-471.
32. Lee, J. M.; Park, H. K; Jung, Y.; Kim, J. K; Jung, S. O.; Chung, B. H., Direct immobilization of protein G variants with various numbers of cysteine residues on a gold surface. *Analytical Chemistry* 2007, 79(7), 2680-2687.

What is claimed is:

1. An assay device for use in determining the presence of a target analyte in a sample, the assay device comprising:
    a solid platform comprising a fibrous mat, the solid platform impregnated with a first FRET chromophore, wherein the first FRET chromophore is not attached to an antibody and further wherein the first FRET chromophore is immobilized within the fibrous mat; and
    an antibody-FRET chromophore conjugate immobilized on a surface of the solid platform, the antibody-FRET chromophore conjugate comprising an antibody affixed to a second FRET chromophore;
    wherein the first FRET chromophore and the second FRET chromophore are selected to provide an energy transfer from one to another when located within a Förster distance with respect to each other, thereby forming a FRET donor-acceptor FRET chromophore pair; and
    wherein the antibody affixed to the second FRET chromophore is configured to position the second FRET chromophore in relation to the first FRET chromophore to perform the energy transfer as a result of a conformational change in the antibody upon capture of a microbial contaminant by the antibody.

2. The assay device of claim 1, wherein the fibrous mat comprises one or both of bacterial cellulose and carboxylated bacterial cellulose.

3. The assay device of claim 1, wherein the first FRET chromophore is a FRET acceptor.

4. The assay device of claim 3, wherein the first FRET chromophore comprises nanoparticles selected from the group consisting of noble metal nanoparticles, gold nanoparticles, and silver nanoparticles.

5. The assay device of claim 4, wherein the first FRET chromophore comprises gold nanoparticles.

6. The assay device of claim 5, wherein the gold nanoparticles are formed within the fibrous mat in situ.

7. The assay device of claim 1, wherein the antibody-FRET chromophore conjugate is immobilized on the fibrous mat with a protein covalently bonded to the fibrous mat.

8. The assay device of claim 7, wherein the protein is bound to an Fc region of the antibody.

9. The assay device of claim 7, wherein the protein is selected from the group consisting of Protein A and Protein A/G.

10. The assay device of claim 1, wherein the second FRET chromophore is a FRET donor.

11. The assay device of claim 10, wherein the second FRET chromophore is selected from the group consisting of a quantum dot and a fluorescent dye.

12. The assay device of claim 1, wherein the antibody is an antibody against a foodborne pathogen.

13. The assay device of claim 1, wherein the antibody is an antibody against a foodborne pathogen selected from the group consisting of *E. coli, Salmonella, Listeria*, and *Campylobacter.*

14. A method of detecting a target analyte in a sample, the method comprising:
    combining the sample with an assay device, the assay device comprising a solid platform comprising a fibrous mat, the solid platform impregnated with a first FRET chromophore, wherein the first FRET chromophore is not attached to an antibody and further wherein the first FRET chromophore is immobilized within the fibrous mat, and an antibody-FRET chromophore conjugate immobilized on a surface of the solid platform, the antibody-FRET chromophore conjugate comprising an antibody affixed to a second FRET chromophore, wherein the first FRET chromophore and the second FRET chromophore are selected to provide an energy transfer from one to another when located within a Förster distance with respect to each other, thereby forming a FRET donor-acceptor chromophore pair, and wherein the antibody affixed to the second FRET chromophore is configured to position the second FRET chromophore in relation to the first FRET chromophore to perform the energy transfer as a result of a conformational change in the antibody upon capture of a microbial contaminant by the antibody; and measuring at least one FRET signal generated by the first FRET chromophore and/or second FRET chromophores to detect the target analyte in the sample.

15. The method of claim 14, wherein the fibrous mat comprises one or both of bacterial cellulose and carboxylated bacterial cellulose.

16. The method of claim 14, wherein the first FRET chromophore is a FRET acceptor.

17. The method of claim 16, wherein the first FRET chromophore comprises nanoparticles selected from the group consisting of noble metal nanoparticles, gold nanoparticles, and silver nanoparticles.

18. The method of claim 17, wherein the first FRET chromophore comprises gold nanoparticles.

19. The method of claim 18, wherein the gold nanoparticles are formed within the fibrous mat in situ.

20. The method of claim 14, wherein the antibody-FRET chromophore conjugate is immobilized on the fibrous mat with a protein covalently bonded to the fibrous mat.

21. The method of claim 20, wherein the protein is bound to an Fc region of the antibody.

22. The method of claim 21, wherein the protein is selected from the group consisting of Protein A and Protein A/G.

23. The method of claim 14, wherein the second FRET chromophore is a FRET donor.

24. The method of claim 23, wherein the second FRET chromophore is selected from the group consisting of a quantum dot and a fluorescent dye.

25. The method of claim 14, wherein the antibody is an antibody against a foodborne pathogen.

26. The method of claim 14, wherein the antibody is an antibody against a foodborne pathogen selected from the group consisting of *E. coli, Salmonella, Listeria,* and *Campylobacter.*

27. A packaging material for detection of microbial contamination in a sample, the packaging material comprising a packaging sheet material and an assay device, the assay device comprising:

a solid platform comprising a fibrous mat, the solid platform impregnated with a first FRET chromophore, wherein the first FRET chromophore is not attached to an antibody and further wherein the first FRET chromophore is immobilized within the fibrous mat; and an antibody-FRET chromophore conjugate immobilized on a surface of the solid platform, the antibody-FRET chromophore conjugate comprising an antibody affixed to a second FRET chromophore;

wherein the first FRET chromophore and the second FRET chromophore are selected to provide an energy transfer from one to another when located within a Förster distance with respect to each other, thereby forming a FRET donor-acceptor chromophore pair, wherein the sample contacts the assay device, and wherein the energy transfer is configured to trigger an optically detectable change in signal in the presence of a microbial contaminant; and wherein the antibody affixed to the second FRET chromophore is configured to position the second FRET chromophore in relation to the first FRET chromophore to perform the energy transfer as a result of a conformational change in the antibody upon capture of a microbial contaminant by the antibody.

28. The packaging material of claim 27, wherein the sample is a food product.

29. The packaging material of claim 27, wherein the packaging sheet material is a polymer film.

* * * * *